US012637695B2

(12) United States Patent
Guilak et al.

(10) Patent No.: US 12,637,695 B2
(45) Date of Patent: May 26, 2026

(54) COMPOSITIONS AND METHODS FOR REGULATING FATTY ACIDS

(71) Applicants:Washington University, St. Louis, MO (US); Shriners Hospitals for Children, Tampa, FL (US)

(72) Inventors: Farshid Guilak, St. Louis, MO (US); Chia-Lung Wu, St. Louis, MO (US); Robert Nims, St. Louis, MO (US); Ruhang Tang, St. Louis, MO (US); Arin Oestreich, St. Louis, MO (US); Natalia Harasymowicz, St. Louis, MO (US)

(73) Assignees: Washington University, St. Louis, MO (US); Shriners Hospitals for Children, Tampa, FL (US)

( * ) Notice: Subject to any disclaimer, the term of this patent is extended or adjusted under 35 U.S.C. 154(b) by 732 days.

(21) Appl. No.: 17/796,585

(22) PCT Filed: Jan. 29, 2021

(86) PCT No.: PCT/US2021/015893
§ 371 (c)(1),
(2) Date: Jul. 29, 2022

(87) PCT Pub. No.: WO2021/155279
PCT Pub. Date: Aug. 5, 2021

(65) Prior Publication Data
US 2023/0059179 A1 Feb. 23, 2023

Related U.S. Application Data

(60) Provisional application No. 62/967,358, filed on Jan. 29, 2020.

(51) Int. Cl.

| | |
|---|---|
| *C12N 15/86* | (2006.01) |
| *A61K 9/00* | (2006.01) |
| *A61K 38/44* | (2006.01) |
| *A61K 48/00* | (2006.01) |
| *C12N 9/02* | (2006.01) |

(52) U.S. Cl.
CPC ............ *C12N 15/86* (2013.01); *A61K 9/0053* (2013.01); *A61K 38/44* (2013.01); *A61K 48/005* (2013.01); *C12N 9/0004* (2013.01); *C12Y 103/01* (2013.01); *A01K 2267/0362* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 6,194,167 B1 * | 2/2001 | Browse ............... | C12N 9/0083 435/468 |
| 2004/0115681 A1 * | 6/2004 | Kang ..................... | A61P 25/00 435/6.12 |

FOREIGN PATENT DOCUMENTS

| | | | |
|---|---|---|---|
| WO | WO 2007/127377 A2 * | 11/2007 | |
| WO | WO 2012/17100 A2 * | 12/2012 | |

OTHER PUBLICATIONS

Medical News Today, https://www.medicalnewstoday.com/articles/248423#types-and-symptoms; accessed on Sep. 24, 2021 (Year: 2021).*
Barhum, https://www.verywellhealth.com/what-is-inflammation-187934, accessed on Sep. 24, 2021 (Year: 2021).*
Naso et al., BioDrugs, 2017; 31:317-334 (Year: 2017).*
Cleveland Clinic, https://my.clevelandclinic.org/health/diseases/5599-osteoarthritis; Oct, 2, 2023 (Year: 2023).*
International Preliminary Report on Patentability for International Application No. PCT/US2021/015893, mailed Aug. 11, 2022, 11 Pages.
International Search Report and Written Opinion for International Application No. PCT/US2021/015893, mailed Apr. 29, 2021, 15 Pages.

* cited by examiner

*Primary Examiner* — Brian Gangle
*Assistant Examiner* — Lakia J Jackson-Tongue
(74) *Attorney, Agent, or Firm* — Polsinelli PC

(57) ABSTRACT

Among the various aspects of the present disclosure relates to methods and compositions useful in convert inflammatory dietary fatty acids (omega 6) to anti-inflammatory fatty acids (omega 3). Specifically, the present disclosure provides methods and compositions for increasing n-3 desaturase expression or activity in a subject. The disclosure provides various compositions for providing increased n-3 desaturase expression or activity including a variety of viral vector and engineered microorganisms. The disclosure provides, in part, methods for reducing local and/or systemic inflammation, improving wound healing, preventing premature cellular senescence, treating or preventing a disease, disorder, or condition related to inflammation or obesity and treating or preventing arthritis.

19 Claims, 13 Drawing Sheets
(8 of 13 Drawing Sheet(s) Filed in Color)
Specification includes a Sequence Listing.

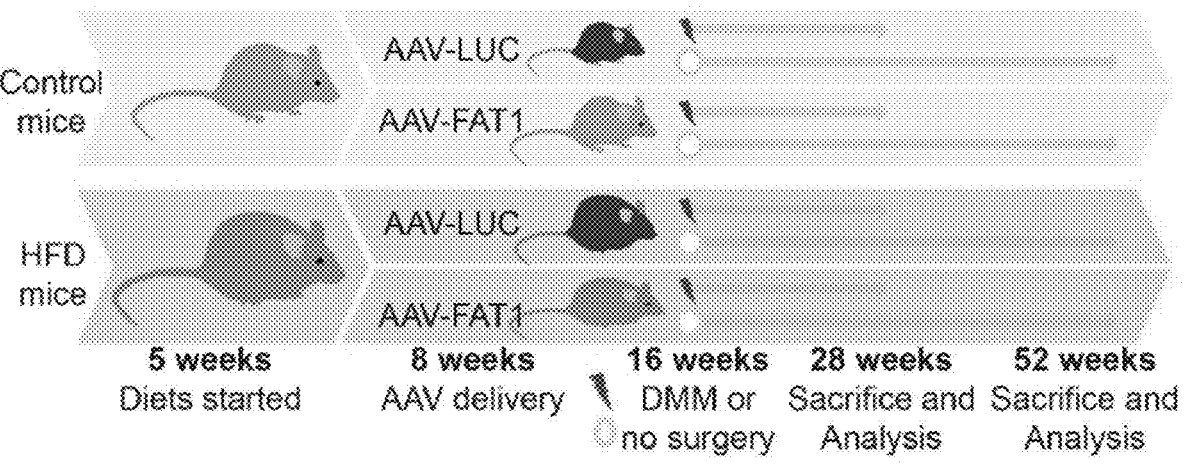
FIG. 5A
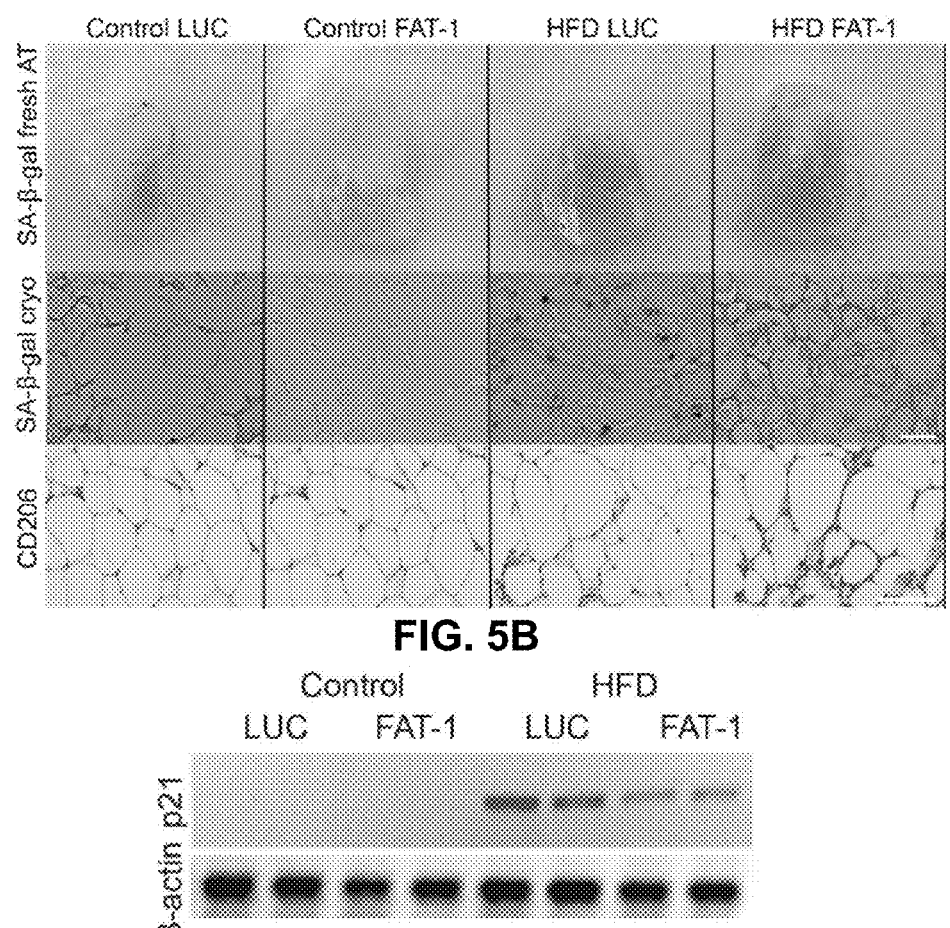
FIG. 5B
FIG. 5C

```
                         SEQUENCE LISTING

<160> NUMBER OF SEQ ID NOS: 2

<210> SEQ ID NO 1
<211> LENGTH: 1209
<212> TYPE: DNA
<213> ORGANISM: Caenorhabditis elegans

<400> SEQUENCE: 1
atggtcgctc attcctcaga agggttatcc gccacggctc cggtcaccgg cggagatgtt      60
ctggttgatg ctcgtgcatc tcttgaagaa aaggaggctc cacgtgatgt gaatgcaaac     120
actaaacagg ccaccactga agagccacgc atccaattac caactgtgga tgctttccgt     180
cgtgcaattc cagcacactg tttcgaaaga gatctcgtta aatcaatcag atatttggtg     240
caagactttg cggcactcac aattctctac tttgctcttc cagcttttga gtactttgga     300
ttgtttggtt acttggtttg gaacattttt atgggagttt ttggattcgc gttgttcgtc     360
gttggacacg attgtcttca tggatcattc tctgataatc agaatctcaa tgatttcatt     420
ggacatatcg ccttctcacc actcttctct ccatacttcc catggcagaa aagtcacaag     480
cttcaccatg ctttcaccaa ccacattgac aaagatcatg gacacgtgtg gattcaggat     540
aaggattggg aagcaatgcc atcatggaaa agatggttca atccaattcc attctctgga     600
tggcttaaat ggttcccagt gtacacttta ttcggtttct gtgatggatc tcacttctgg     660
ccatactctt cactttttgt tcgtaactct gaacgtgttc aatgtgtaat ctctggaatc     720
tgttgctgtg tgtgtgcata tattgctcta acaattgctg gatcatattc caattggttc     780
tggtactatt gggttccact ttctttcttc ggattgatgc tcgtcattgt tacctatttg     840
caacatgtcg atgatgtcgc tgaggtgtac gaggctgatg aatggagctt cgtccgtgga     900
caaacccaaa ccatcgatcg ttactatgga ctcggattgg acacaacgat gcaccatatc     960
acagacggac acgttgccca tcacttcttc aacaaaatcc cacattacca tctcatcgaa    1020
gcaaccgaag gtgtcaaaaa ggtcttggag ccgttgtccg acacccaata cgggtacaaa    1080
tctcaagtga actacgattt ctttgcccgt ttcctgtggt tcaactacaa gctcgactat    1140
ctcgttcaca agaccgccgg aatcatgcaa ttccgaacaa ctctcgagga gaaggcaaag    1200
gccaagtaa                                                            1209

<210> SEQ ID NO 2
<211> LENGTH: 402
<212> TYPE: PRT
<213> ORGANISM: Caenorhabditis elegans
```

-continued

<400> SEQUENCE: 2

```
Met Val Ala His Ser Ser Glu Gly Leu Ser Ala Thr Ala Pro Val Thr
1               5                   10                  15

Gly Gly Asp Val Leu Val Asp Ala Arg Ala Ser Leu Glu Glu Lys Glu
                20                  25                  30

Ala Pro Arg Asp Val Asn Ala Asn Thr Lys Gln Ala Thr Thr Glu Glu
            35                  40                  45

Pro Arg Ile Gln Leu Pro Thr Val Asp Ala Phe Arg Arg Ala Ile Pro
        50                  55                  60

Ala His Cys Phe Glu Arg Asp Leu Val Lys Ser Ile Arg Tyr Leu Val
65                  70                  75                  80

Gln Asp Phe Ala Ala Leu Thr Ile Leu Tyr Phe Ala Leu Pro Ala Phe
                85                  90                  95

Glu Tyr Phe Gly Leu Phe Gly Tyr Leu Val Trp Asn Ile Phe Met Gly
            100                 105                 110

Val Phe Gly Phe Ala Leu Phe Val Val Gly His Asp Cys Leu His Gly
            115                 120                 125

Ser Phe Ser Asp Asn Gln Asn Leu Asn Asp Phe Ile Gly His Ile Ala
        130                 135                 140

Phe Ser Pro Leu Phe Ser Pro Tyr Phe Pro Trp Gln Lys Ser His Lys
145                 150                 155                 160

Leu His His Ala Phe Thr Asn His Ile Asp Lys Asp His Gly His Val
                165                 170                 175

Trp Ile Gln Asp Lys Asp Trp Glu Ala Met Pro Ser Trp Lys Arg Trp
            180                 185                 190

Phe Asn Pro Ile Pro Phe Ser Gly Trp Leu Lys Trp Phe Pro Val Tyr
            195                 200                 205

Thr Leu Phe Gly Phe Cys Asp Gly Ser His Phe Trp Pro Tyr Ser Ser
        210                 215                 220

Leu Phe Val Arg Asn Ser Glu Arg Val Gln Cys Val Ile Ser Gly Ile
225                 230                 235                 240

Cys Cys Cys Val Cys Ala Tyr Ile Ala Leu Thr Ile Ala Gly Ser Tyr
                245                 250                 255

Ser Asn Trp Phe Trp Tyr Tyr Trp Val Pro Leu Ser Phe Phe Gly Leu
            260                 265                 270

Met Leu Val Ile Val Thr Tyr Leu Gln His Val Asp Asp Val Ala Glu
            275                 280                 285

Val Tyr Glu Ala Asp Glu Trp Ser Phe Val Arg Gly Gln Thr Gln Thr
        290                 295                 300

Ile Asp Arg Tyr Tyr Gly Leu Gly Leu Asp Thr Thr Met His His Ile
305                 310                 315                 320

Thr Asp Gly His Val Ala His His Phe Phe Asn Lys Ile Pro His Tyr
                325                 330                 335

His Leu Ile Glu Ala Thr Glu Gly Val Lys Lys Val Leu Glu Pro Leu
            340                 345                 350

Ser Asp Thr Gln Tyr Gly Tyr Lys Ser Gln Val Asn Tyr Asp Phe Phe
        355                 360                 365
```

-continued

```
Ala Arg Phe Leu Trp Phe Asn Tyr Lys Leu Asp Tyr Leu Val His Lys
    370             375             380

Thr Ala Gly Ile Met Gln Phe Arg Thr Thr Leu Glu Glu Lys Ala Lys
385             390             395             400

Ala Lys
```

COMPOSITIONS AND METHODS FOR REGULATING FATTY ACIDS

CROSS-REFERENCE TO RELATED APPLICATION

This application claims benefit from International Application Serial number PCT/US2021/015893, filed Jan. 29, 2021, which claims the benefit of U.S. Provisional Application Ser. No. 62/967,358 filed on Jan. 29, 2020, which is incorporated herein by reference in its entirety.

GOVERNMENTAL RIGHTS

This invention was made with government support under AG046927 awarded by the National Institutes of Health. The government has certain rights in the invention.

FIELD OF THE TECHNOLOGY

The present disclosure relates generally to the fields of metabolism, inflammation and medicine. Specifically, the present disclosure relates to methods and compositions for altering the content of polyunsaturated fatty acids in a subject, including, reducing fatty acids, such as omega-6, in mammals.

BACKGROUND

The worldwide trend of increased saturated fat and carbohydrate consumption along with increased omega-6 (n-6) and decreased omega-3 (n-3) fatty acid intake has coincided with the growing prevalence of chronic, life-threatening diseases, suggesting a critical link between the shift in our dietary composition and today's health epidemic. Saturated fats can be readily produced from carbohydrates in mammals, and both saturated fats and carbohydrates are highly abundant in the modern Western diet; in contrast, omega-3 fatty acids cannot be made de novo nor converted from other nutrients in mammals, and therefore must be obtained from dietary sources (e.g., fish oil).

Normally, mammals readily obtain saturated fatty acids (SFA) from either the diet or endogenous synthesis from glucose or amino acids, and monounsaturated fatty acids (MUFA) can also be obtained from the diet or converted from SFA by the stearoyl-CoA desaturase-1 (SCD-1) gene. On the other hand, n-6 and n-3 polyunsaturated fatty acids (PUFA) cannot be inter-converted or synthesized de novo in mammals and are mainly acquired through the diet. In this context, to increase the tissue content of essential fatty acids, they must be supplemented in the diet, such as adding vegetable oils (e.g., corn, soybean, safflower, etc.) for n-6 PUFA or fish oil for n-3 PUFA.

The high fat diet has been widely investigated for its role in the development of metabolic diseases. However, the interpretation of results from these reports often does not recognize the different types of fats—including saturated fatty acids (SFA), monounsaturated fatty acids (MUFA), n-6 polyunsaturated fatty acids (PUFA), and n-3 PUFA and their differential effects to study outcomes. In addition, comparative nutrition studies conventionally utilize diets with different fat sources, introducing other variables that can become confounding factors. For example, the presence of many other components, other than n-6 or n-3 fatty acids, in the supplemented oils makes it difficult to interpret the experimental outcome for the authentic effect of n-6 or n-3 fatty acids. By overlooking or failing to isolate the respective impact of specific fats, the existing research has often presented inconsistent or contradicting conclusions, causing confusion among scientists and the public alike.

There remains a need in the art for additional compositions and methods for altering the content of polyunsaturated fatty acids in a subject.

SUMMARY

Among the various aspects of the present disclosure is the provision of a methods and compositions for reducing fatty acids (e.g., omega-6) in a subject.

An aspect of the present disclosure provides for a method of converting omega-6 fatty acid to omega-3 fatty acid or reducing omega-6:omega-3 ratio in a subject comprising: delivering a fat-1 gene via viral vector (e.g., AAV) or delivering the fat-1 gene via non-pathogenic bacteria (e.g., engineered probiotic) in the natural gut microbiome (e.g., gut, skin oral cavity or vaginal tissues), without genome editing of the subject or cells of the subject. Another aspect of the present disclosure provides for a method of treating or preventing an omega-6 associated disease, disorder, or condition (e.g., musculoskeletal disease, reproductive dysfunction, cardiovascular disease, obesity, joint disease (e.g., arthritis), inflammation) in a subject comprising: delivering a fat-1 gene via viral vector (e.g., AAV) or delivering the fat-1 gene via non-pathogenic bacteria (e.g., probiotic) in the gut microbiome, without genome editing of the subject or cells of the subject. Another aspect of the present disclosure provides for a method of increasing fat-1 gene expression in a subject comprising: delivering a fat-1 gene via viral vector (e.g., AAV) or increasing fat-1 activity by delivering the fat-1 gene via non-pathogenic bacteria (e.g., engineered probiotic) in the gut microbiome, without genome editing of the subject or cells of the subject.

Another aspect of the present disclosure provides for a method of delivering fat-1 gene to a subject comprising administering engineered bacteria having a fat-1 gene engineered into the bacterial cell genome. Another aspect of the present disclosure provides for a method of delivering the fat-1 gene to a cell, animal, or human wherein the fat-1 gene is being delivered via a viral vector (e.g., AAV).

Another aspect of the present disclosure provides for a subject, wherein the subject has an increased level of omega-3 fatty acid content or reduced omega-6 fatty acid content compared to a wild type subject, wherein the subject is genetically engineered to incorporate the fat-1 gene into the mammal's cells or is administered a probiotic engineered to incorporate the fat-1 gene. In some embodiments, the bacteria is a non-pathogenic bacteria are engineered to express fat-1. In some embodiments, the non-pathogenic bacteria are transformed with nucleic acids coding for fat-1 gene to generate synthetic probiotics. In some embodiments, the engineered probiotic comprises one or more of: *Escherichia, Lactobacillus, Bifidobacterium, Lactococcus, Bacteroides, Clostridium,* and *Streptococcus*. In some embodiments, the nucleic acid sequence coding for fat-1 may comprise additional nucleic acid sequences which code for antibiotic selection, genetic activation, stability, and/or survival.

In some embodiments, the subject has a reproductive health condition, metabolic health condition (e.g., obesity), or a musculoskeletal condition (e.g., osteoarthritis (OA)). In some embodiments, the subject is a human, livestock, or companion animal.

Other objects and features will be in part apparent and in part pointed out hereinafter.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 2A shows the gene delivery of Fat-1 compared to luciferase (LUC) via pAAV8 and mice injected with AAV8-Luc in the tail vein show broad delivery throughout the body. FIG. 2B is a diagram showing the study design. FIG. 2C is a graph showing weight in control versus HFD mice. FIG. 2D is a graph showing adipose tissue in control versus HFD mice. FIG. 2E is a graph showing serum cytokine levels in control versus HFD mice. N-15 per group. Groups not sharing a letter are significantly different from another.

FIG. 3A shows representative safranin-O, fast green staining of DMM-joints in control and HFD mice. FIG. 3B shows the total Mankin score between control and HFD mice. FIG. 3C shows the synovitis score for right and left joints in control and HFD mice. FIG. 3D shows representative H&E staining of DMM-joints in control and HFD mice. FIG. 3E shows representative 3D reconstructions of DMM-joints in control and HFD mice. FIG. 3F shows BV/TV, Tb.N in tibia metaphysis of DMM-joints in control and HFD mice. n=15 per group. Groups not sharing a letter are significantly different from one another.

FIG. 4A shows representative flow cytometry gating strategy for CD45$^+$CD11b$^+$ cells from epididymal adipose tissue. FIG. 4B shows the percentage of CD45$^+$CD11b$^+$CD11c$^+$ (M1-like) cells. FIG. 4C shows the percentage of CD45$^+$CD11b$^+$CD301$^+$ (M2-like) cells. FIG. 4D shows the percentage of CD45$^+$CD11b$^+$CD206$^+$ (M2-like) cells. Groups not sharing a letter are significantly different from one another.

FIG. 5A-5C show AAV8-fat-1 overexpression significantly reduced obesity-induced cell senescence, indicated by decreased content of β-gal positive cells and decreased expression of p21 protein in AT. FIG. 5A shows the study design and timeline. FIG. 5B shows representative senescence-associated-β-galactosidase staining of fresh and cryosectioned adipose tissue (AT) and CD206 IHC of paraffin section of AT. Scale bars—100 μM. FIG. 5C shows anti-p21 and anti-β-actin western blot analysis from AT.

FIG. 7A shows the in vitro study design. FIG. 7B shows the fluorescence intensity of ROS measured by DCFDA assay. FIG. 7C shows representative ROS production, p16INK4a expression, and SA-β-gal expression in primary chondrocytes treated with conditioned media collected from bone marrow macrophages from Control or HFD mice expressing fat-1 or LUC genes (Control/HFD/LUC/FAT1). scale bars=400 μm

DETAILED DESCRIPTION

Figure 1A:
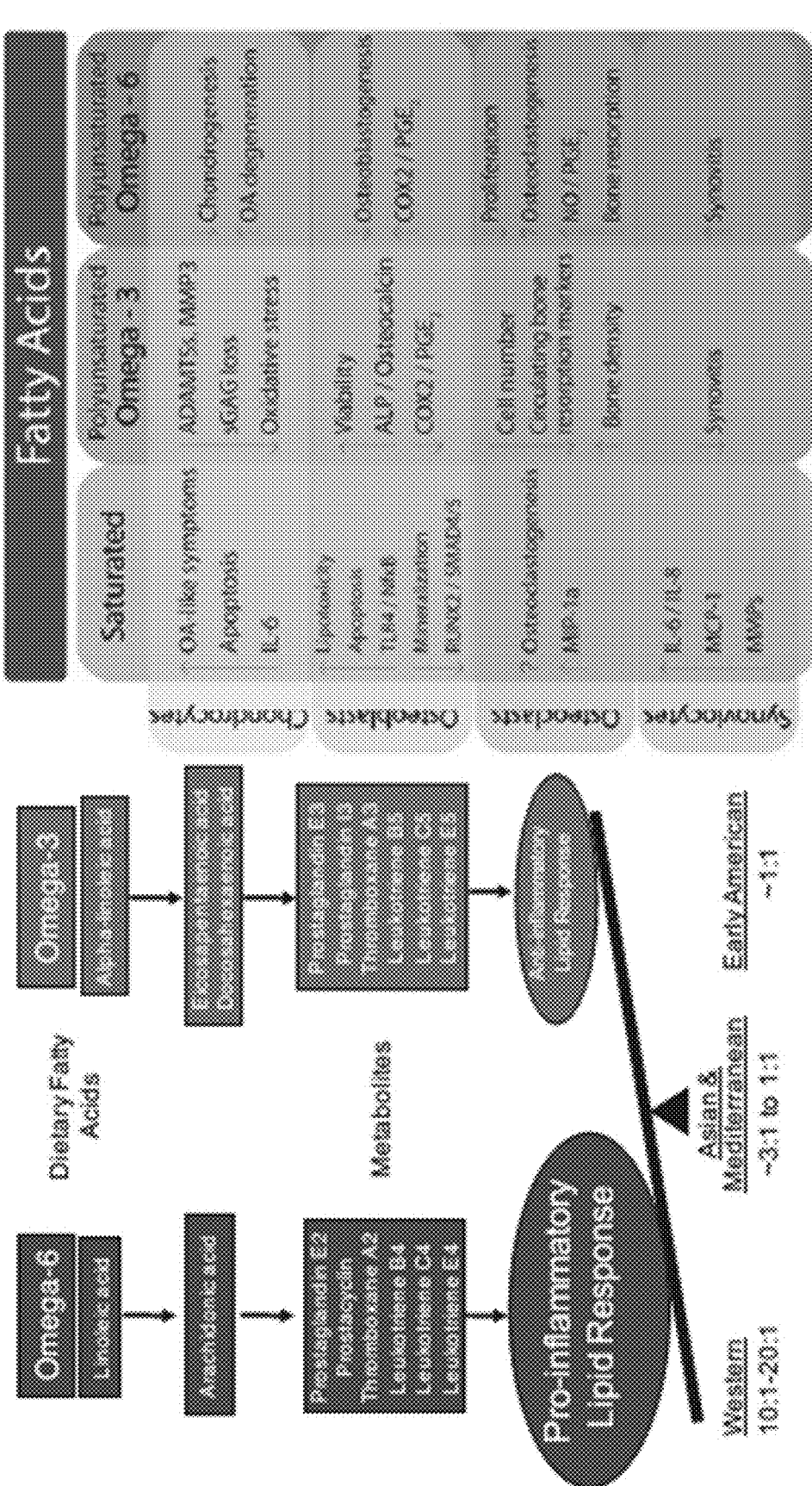
FIG. 1A is a diagram showing the relative amounts of dietary ω-6:ω-3 fatty acids can mediate inflammation via various eicosanoids. A balanced fatty-acid ω-6:ω-3 is less inflammatory than an ω-6-rich diet. The effects of fatty acids on joint cells. Saturated fats, ω-3 PUFAs, and ω-6 PUFAs can have differing effects on various cells of the joint. In chondrocytes, high-levels of SFAs and ω-6 PUFAs have negative effects on cartilage, increasing OA, joint degeneration, cellular senescence, and cell death, while ω-3 PUFAs can have beneficial effects on cartilage degradation, synovitis, and pro-inflammatory mediators.

The present disclosure is based, at least in part, that the *C. elegans* n-3 desaturase gene, fat-1, can be successfully introduced into other types of animal cells (e.g., the cells of mammals, birds, and fish), where it quickly and effectively elevates the cellular n-3 PUFA content and modulates the ratio of n-6:n-3 PUFAs. For example, the present disclosure provides that by increasing expression or activity of fat-1 in a subject is capable of reducing systemic metabolic inflammation. Moreover, increased expression or activity of fat-1 correlated with reduced adiposity, body mass, improved bone microstructure and reduced the severity of post-traumatic osteoarthritis. In addition, in the context of obesity and osteoarthritis, increased expression or activity of fat-1 increased the number of anti-inflammatory macrophages and prevented premature cellular senescence.

Accordingly, the present disclosure provides compositions and methods to deliver fat-1 to animals and humans, in some embodiments, eliminating the need to genetically modify germ cells or embryos to create transgenic animals. In one aspect, the fat-1 gene can be delivered using viral gene therapy to specific tissues or systemically. In another aspect, an engineered gut microbiome via probiotic bacteria is used to provide the subject with elevated fat-1 activity. Increased fat-1 expression and/or activity improves health of companion animals, livestock, and humans.

The present disclosure provides for the use of the fat-1 transgene is delivered in some embodiment via probiotics or adeno-associated virus (AAV) injection to increase omega-3 fatty acid levels systemically or to targeted joints. This is accomplished by, in part, Fat-1 gene mediated conversion of proinflammatory omega-6 fatty acids, commonly consumed in Western diets, to anti-inflammatory omega-3 fatty acids.

The methods and compositions disclosed herein can be applied to prevent or treat companion animals for common inflammatory diseases, such as osteoarthritis (OA), or to produce healthy omega-3 rich animal products for human consumption by treatment of livestock. For example, the engineered probiotic can be added to pet and livestock feed. Once ingested the probiotic is allowed to colonize and expand within the subject thereby elevating the activity of fat-1 in the gut of the subject and increases the levels of omega-3 in the subject.

A composition of the disclosure may further comprise a pharmaceutically acceptable excipient, carrier, or diluent. Further, a composition of the disclosure may contain preserving agents, solubilizing agents, stabilizing agents, wetting agents, emulsifiers, salts (substances of the present disclosure may themselves be provided in the form of a pharmaceutically acceptable salt), buffers, coating agents, or antioxidants.

Other aspects and iterations of the disclosure are described more thoroughly below.

I. Compositions (a) n-3 Desaturase Nucleic Acids and Peptides

The present disclosure provides compositions useful for increasing the expression and/or activity of fat-1 in a subject. In some embodiments, the compositions comprise nucleic acids encoding a fat-1 n-3 fatty acid desaturase. As shown in the examples below, recombinant adenoviral expression vectors can mediate fat-1 gene transfer in vivo or in vitro. Thus, the present disclosure encompasses adenoviral vectors expressing an omega-3 desaturase (e.g., fat-1), or biologically active variants thereof (e.g., codon optimized sequences), as well as other types of viral and non-viral expression vectors. More specifically, the disclosure includes a nucleic acid molecules that include a sequence encoding an enzyme that desaturates an n-6 to a corresponding n-3 fatty acid. In some embodiments, the desaturase in encoded by the *C. elegans* fat-1 gene sequence of atggtcgctc attcctcaga agggttatcc gccacggctc cggtcaccgg cggagatgtt ctggttgatg ctcgtgcatc tcttgaagaa aaggaggctc cacgtgatgt gaatgcaaac actaaacagg ccaccactga agagccacgc atccaattac caactgtgga tgctttccgt cgtgcaattc cagcacactg tttcgaaaga gatctcgtta aatcaatcag atatttggtg caagactttg cggcactcac aat- tctctac tttgctcttc cagcttttga gtactttgga ttgtttggtt acttggtttg gaacatttt atgggagttt ttggattcgc gttgttcgtc gttggacacg attgtcttca tggatcattc tctgataatc agaatctcaa tgatttcatt gga- catatcg ccttctcacc actcttctct ccatacttcc catggcagaa aagt- cacaag cttcaccatg ctttcaccaa ccacattgac aaagatcatg gacacgtgtg gattcaggat aaggattggg aagcaatgcc atcatggaaa agatggttca atccaattcc attctctgga tggcttaaat ggttcccagt gta- cacttta ttcggtttct gtgatggatc tcacttctgg ccatactctt cacttttgt tcgtaactct gaacgtgttc aatgtgtaat ctctggaatc tgttgctgtg tgtgtg- cata tattgctcta acaattgctg gatcatattc caattggttc tggtactatt gggttccact ttctttcttc ggattgatgc tcgtcattgt tacctatttg caa- catgtcg atgatgtcgc tgaggtgtac gaggctgatg aatggagctt cgtccgtgga caaacccaaa ccatcgatcg ttactatgga ctcggattgg acacaacgat gcaccatatc acagacggac acgttgccca tcacttcttc aacaaaatcc cacattacca tctcatcgaa gcaaccgaag gtgtcaaaaa ggtcttggag ccgttgtccg acacccaata cgggtacaaatctcaagtga act- acgattt ctttgcccgt ttcctgtggt tcaactacaa gctcgactatctcgttcaca agaccgccgg aatcatgcaa ttccgaacaa ctctcgagga gaaggcaaaggc- caagtaa (SEQ ID NO:1). The *C. elegans* fat-1 gene encodes a polypeptide having the amino acid sequence

```
                                           (SEQ ID NO: 2)
MVAHSSEGLSATAPVTGGDVLVDARASLEEKEAPRDVNANTKQATTEEPR

IQLPTVDAFRRAIPAHCFERDLVKSIRYLVQDFAALTILYFALPAFEYFG

LFGYLVWNIFMGVFGFALFVVGHDCLHGSFSDNQNLNDFIGHIAFSPLFS

PYFPWQKSHKLHHAFTNHIDKDHGHVWIQDKDWEAMPSWKRWFNPIPFSG

WLKWFPVYTLFGFCDGSHFWPYSSLFVRNSERVQCVISGICCCVCAYIAL

TIAGSYSNWFWYYWVPLSFFGLMLVIVTYLQHVDDVAEVYEADEWSFVRG

QTQTIDRYYGLGLDTTMHHITDGHVAHHFFNKIPHYHLIEATEGVKKVLE

PLSDTQYGYKSQVNYDFFARFLWFNYKLDYLVHKTAGIMQFRTTLEEKAK

AK.
```

In some embodiments, sequences encoding other desaturases can be included in the nucleic acid constructs of the disclosure and used in the methods described herein. For example, the encoded desaturase can be that of a plant, a nematode other than *C. elegans*, cyanobacteria, or EPA-rich fungi (e.g., *Saprolegnia diclina*). Other fungi that can supply the desaturase sequence include *Saccharomyces kluyveri* and *Saprolegnia diclina*. Thus, the disclosure features nucleic acid molecules comprising a sequence encoding an n-3 desaturase operably linked to a regulatory element (e.g., a constitutively active or tissue-specific promoter). Specific promoters are known in the art and are described further below.

The sequence encoding the n-3 desaturase can include at least one optimized codon. The number of codons that are optimized can vary. Preferably, the number is sufficient to improve some aspect of expression (e.g., the number of copies transcribed) or to otherwise enhance the utility of the sequence. In some instances, modifying only a few codons (e.g., 1-5) can improve the sequence. In other instances, a larger number of codons (e.g., at least 5 and up to 150) can be optimized. In specific embodiments, and regardless of the initial source of the desaturase-encoding sequence, a nucleic acid molecule can include 5-10, 10-15, 15-20, 20-25, 25-30, 30-35, 35-40, 40-45, 45-50, 50-55, 55-60, 60-65, 65-70, 70-75, 75-80, 80-85, 85-90, 90-95, 95-100, 100-105, 105-110, 110-115, 115-120, 120-125, 125-130, 130-135, 135-140, 140-145, 145-150, 10-125, 25-100, 30-90, 40-80, 50-70, or about 60 optimized codons.

Moreover, the positions of the optimized codons can vary. With respect to the *C. elegans* fat-1 gene, an optimized codon can be found at one or more of position 6, 9, 18, 20, 22, 24, 28-30, 33-36, 47, 49, 52, 54, 58, 60, 61, 64, 67, 69-71, 73, 77, 79, 81, 86, 89, 92, 94-95, 100, 101, 105, 106, 112, 115, 118, 124, 127, 128, 131, 146, 151, 154, 161, 163, 25 164, 169, 178, 187, 188, 195, 197, 200, 202, 206, 210, 214, 217, 221, 223, 225, 227, 228, 232, 234, 241, 245, 255, 271, 280-282, 284, 285, 301, 303, 310, 312, 327, 362, or 370. Where desaturase-encoding genes other than the *C. elegans* fat-1 gene are used, codons can be optimized at one or more (including all) of these same positions. In homologous genes (e.g., an n-3 desaturase gene of a plant or fungus), the positions optimized can be those corresponding to the positions listed above.

As noted above, some of the nucleic acid molecules of the disclosure may be referred to as "isolated". That qualifier is not considered necessary, however, when the nucleic acid sequence is not a naturally occurring sequence. As sequences that have been optimized (particularly those in which several codons have been optimized) are highly unlikely to occur in nature, we do not see a need to refer to these sequences as "isolated". Thus, while a nucleic acid molecule that is a naturally occurring sequence must be "isolated" (separated from some, most, or all of the components with which it is associated in its natural environment), nucleic acid molecules that are not naturally occurring (e.g., nucleic acids having an unnatural optimized sequence) need not be designated as isolated.

In addition to regulatory elements and desaturase-encoding sequences, the nucleic acid molecules can include a sequence that encodes a polypeptide that confers a benefit upon a subject to whom it is administered (e.g., a therapeutic polypeptide) or that improves the utility of the molecule in an assay (e.g., a second sequence can encode a marker protein). Examples of fluorescent (e.g., GFP and EGFP) are provided herein, as are examples of non-fluorescent marker (e.g., β-galactosidase). Other marker or "reporter" proteins are known and routinely used in the art and can also be incorporated in the nucleic acid constructs described herein.

The nucleic acid molecules can be, or can be a part of, a vector (e.g., an expression vector). We noted our use of adenoviral vectors above (see also, the Examples). Other viral vectors that can be employed as expression constructs in the present invention include vectors derived from viruses such as vaccinia virus (e.g., a pox virus or a modified vaccinia virus ankara (MVA)), an adeno-associated virus (AAV), or a herpes virus. These viruses offer several attractive features for use in connection with animal cells, including human cells. For example, herpes simplex viruses (e.g., HSV-1) can be selected to deliver a desaturase (e.g., fat-1 or a homologue thereof (or biologically active variants, including codon-optimized variants)) to neuronal cells. Such vectors are useful, for example, in treating or preventing neurodegenerative conditions.

Retroviruses, liposomes, and plasmid vectors are also well known in the art and can also be used to deliver an n-3 desaturase-encoding sequence to a cell (e.g., the expression vector pU 78 can be used when one wishes to fuse a desaturase-encoding (e.g., fat-1) sequence to the lacZ gene; lacZ encodes the detectable marker β-galactosidase.

As noted, a desaturase-encoding sequence (e.g. a fat-1 sequence) or a biologically active variant thereof (including a codon optimized sequence) can also be fused to other types of heterologous sequences, such as a sequence that encodes another therapeutic gene or a sequence that, when expressed, improves the quantity or quality (e.g., solubility or circulating half-life) of the fusion protein. For example, pGEX vectors can be used to express the proteins of the invention fused to glutathione S-transferase (GST). In general, such fusion proteins are soluble and can be readily purified from lysed cells by adsorption to glutathione-agarose beads followed by elution in the presence of free glutathione. The pGEX vectors (Pharmacia Biotech Inc; Smith and Johnson, Gene 67:31-40, 1988) are designed to include thrombin or factor Xa protease cleavage sites so that the cloned target gene product can be released from the GST moiety. Other fusion partners include albumin and a region (e.g., the Fc region, with or without the hinge region) of an immunoglobulin molecule (e.g., IgG, IgA, IgM, or IgE). Other useful vectors include pMAL (New England Biolabs, Beverly, Mass.) and pRIT5 (Pharmacia, Piscataway, N.J.), which fuse maltose E binding protein and protein A, respectively, to an n-3 desaturase.

Transgene expression can be sufficiently prolonged from episomal systems, so that re-administration of any given expression vector, with its transgene, is not necessary. Alternatively, the vector can be designed to promote integration into the host genome, preferably in a site-specific location, which would help ensure that the transgene is not lost during the cell's lifetime. Whatever the means of delivery, transcriptional control, exerted by the host cell, would promote tissue specificity and regulate transgene expression. Accordingly, the nucleic acid molecules of the invention can include sequences that promote integration of a desaturase-encoding sequence into a host's genome.

The expression vector will be selected or designed depending on, for example, the type of host cell to be transformed and the level of protein expression desired. For example, when the host cells are mammalian cells, the expression vector can include viral regulatory elements, such as promoters derived from polyoma, Adenovirus 2, cytomegalovirus and Simian Virus 40. These regulatory elements can be used with non-mammalian (e.g., avian or fish) cells as well. The nucleic acid inserted (i.e., the sequence to be expressed; here, an n-3 desaturase, such as that encoded by fat-1) can also be modified to encode residues that are preferentially utilized in *E. coli* (Wada et al., Nucleic Acids Res. 20:2111-2118, 1992). Similarly, one can preferentially modify codons, if necessary or desired, in organisms other than *E. coli*. Modifications such as these (e.g., incorporation of various regulatory elements and codon optimization) can be achieved by standard recombinant techniques. More generally, the expression vectors of the disclosure can be designed to express proteins in prokaryotic or eukaryotic cells. For example, polypeptides of the disclosure can be expressed in bacterial cells (e.g., *E. coli*), fungi, yeast, or insect cells (e.g., using baculovirus expression vectors). For example, a baculovirus such as *Autographa califomica* nuclear polyhedrosis virus (AcNPV), which grows in *Spodoptera frugiperda* cells, can be used as a vector to express an n-3 desaturase.

The vectors and other nucleic acid molecules of the disclosure (e.g., the fat-1 cDNA per se) can also include sequences that limit the temporal expression of the transgene. For example, the transgene can be controlled by drug inducible promoters by, for example, including a cAMP response element (CRE) enhancer in a promoter and treating the transfected or infected cell with a cAMP modulating drug (Suzuki et al., Hum. Gene Ther. 7:1883-1893, 1996). Alternatively, repressor elements can prevent transcription in the presence of the drug (Hu et al., Cancer Res. 57:3339-3343, 1997). Spatial control of expression has also been achieved by using ionising radiation (radiotherapy) in conjunction with the erg1 gene promoter. Constructs that contain such regulatory sequences are within the scope of the present disclosure.

The nucleic acid segments used in the present disclosure, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

The nucleic acid used in the present disclosure encodes an n-3 desaturase. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by human may be introduced through the application of site-directed mutagenesis techniques, e.g., to introduce improvements to the antigenicity of the protein.

Suitable methods for nucleic acid delivery to effect expression of compositions of the present disclosure are believed to include virtually any method by which a nucleic acid (e.g., DNA, including viral and nonviral vectors) can be introduced into a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium* mediated transformation (U.S. Pat. Nos. 5,591,616 and 5,563,055, each incorporated herein by reference); by PEG mediated transformation of protoplasts (Omirulleh et al., 1993; U.S. Pat. Nos. 4,684,611 and 4,952,500, each incorporated herein by reference); or by desiccation/inhibition mediated DNA uptake (Potrykus et al., 1985). Through the application of techniques such as these, organelle(s), cell(s), tissue(s) or organism(s) may be stably or transiently transformed.

The term "functionally equivalent codon" is used herein to refer to codons that encode the same amino acid, such as the six codons for arginine or serine, and also refers to codons that encode biologically equivalent amino acids.

It also will be understood that amino acid and nucleic acid sequences may include additional residues, such as additional N- or C-terminal amino acids, or 5' or 3' sequences, respectively, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in an amino acid sequence, and in its underlying DNA coding sequence, and nevertheless produce a protein with like properties. It is thus contemplated by the inventors that various changes may be made in the DNA sequences of genes or nucleic acids without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. It is understood that an amino acid can be substituted for another having a similar hydrophilicity value and still produce a biologically equivalent and immunologically equivalent protein.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known and include: arginine and lysine; glutamate and aspartate; serine and threonine; glutamine and asparagine; and valine, leucine and isoleucine.

In certain embodiments, a desaturase of the disclosure comprises the sequence set forth in SEQ ID NO:2. In other embodiments, an n-3 desaturase of the disclosure may have about 80% identity to SEQ ID NO: 2. For example, a desaturase a of the disclosure may have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity to SEQ ID NO: 1. In particular, "percent identity" of two polypeptides or two nucleic acid sequences is determined using the algorithm of Karlin and Altschul (Proc. Natl. Acad. Sci. USA 87:2264-2268, 1993). Such an algorithm is incorporated into the BLASTN and BLASTX programs of Altschul et al. (J. Mol. Biol. 215:403-410, 1990). BLAST nucleotide searches may be performed with the BLASTN program to obtain nucleotide sequences homologous to a nucleic acid molecule of the disclosure. Equally, BLAST protein searches may be performed with the BLASTX program to obtain amino acid sequences that are homologous to a polypeptide of the disclosure. To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (e.g., BLASTX and BLASTN) are employed.

In many instances, a biologically active variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present disclosure and still obtain a functional molecule that encodes a variant or derivative polypeptide with desirable characteristics. When it is desired to alter the amino acid sequence of a polypeptide to create an equivalent, or even an improved, variant or portion of a polypeptide described herein, one skilled in the art will typically change one or more of the codons of the encoding DNA sequence.

The nucleic acid sequences which encode a desaturase of the disclosure can be operatively linked to expression control sequences. "Operatively linked" refers to a juxtaposition wherein the components so described are in a relationship permitting them to function in their intended manner. An expression control sequence operatively linked to a coding sequence is achieved under conditions compatible with the expression control sequences. As used herein, the expression control sequences refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, and maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

In one aspect, the present disclosure provides for a vector comprising a nucleic acid sequence encoding a desaturase of the disclosure. In one aspect, the present disclosure is predicated, at least in part, on the ability of adeno-associated virus (AAV) vectors to be safely administered to humans and to provide persistent expression of a therapeutic transgene. The disclosure provides an adeno-associated virus (AAV) vector which comprises, consists essentially of, or consists of a nucleic acid sequence encoding a desaturase polypeptide. When the AAV vector consists essentially of a nucleic acid sequence encoding a desaturase polypeptide, additional components can be included that do not materially affect the AAV vector (e.g., genetic elements such as poly(A) sequences or restriction enzyme sites that facilitate manipulation of the vector in vitro). When the AAV vector consists of a nucleic acid sequence encoding a desaturase polypeptide, the AAV vector does not comprise any additional components (i.e., components that are not endogenous to AAV and are not required to effect expression of the nucleic acid sequence to thereby provide the desaturase).

Adeno-associated virus is a member of the Parvoviridae family and comprises a linear, single-stranded DNA genome of less than about 5,000 nucleotides. AAV requires co-infection with a helper virus (i.e., an adenovirus or a herpes virus), or expression of helper genes, for efficient replication. AAV vectors used for administration of therapeutic nucleic acids typically have approximately 96% of the parental genome deleted, such that only the terminal repeats (ITRs), which contain recognition signals for DNA replication and packaging, remain. This eliminates immunologic or toxic side effects due to expression of viral genes. In addition, delivering specific AAV proteins to producing cells enables integration of the AAV vector comprising AAV ITRs into a specific region of the cellular genome, if desired (see, e.g., U.S. Pat. Nos. 6,342,390 and 6,821,511). Host cells comprising an integrated AAV genome show no change in cell growth or morphology (see, for example, U.S. Pat. No. 4,797,368).

The AAV ITRs flank the unique coding nucleotide sequences for the non-structural replication (Rep) proteins and the structural capsid (Cap) proteins (also known as virion proteins (VPs)). The terminal 145 nucleotides are self-complementary and are organized so that an energetically stable intramolecular duplex forming a T-shaped hairpin may be formed. These hairpin structures function as an origin for viral DNA replication by serving as primers for the cellular DNA polymerase complex. The Rep genes encode the Rep proteins Rep78, Rep68, Rep52, and Rep40. Rep78 and Rep68 are transcribed from the p5 promoter, and Rep 52 and Rep40 are transcribed from the p19 promoter. The Rep78 and Rep68 proteins are multifunctional DNA binding proteins that perform helicase and nickase functions during productive replication to allow for the resolution of AAV termini (see, e.g., Im et al., Cell, 61: 447-57 (1990)). These proteins also regulate transcription from endogenous AAV promoters and promoters within helper viruses (see, e.g., Pereira et al., J. Virol., 71: 1079-1088 (1997)). The other Rep proteins modify the function of Rep78 and Rep68. The cap genes encode the capsid proteins VP1, VP2, and VP3. The cap genes are transcribed from the p40 promoter. In a particular embodiment, the AAV contains a pair of inverted terminal repeats (ITRs) which flank at least one cassette containing a promoter which directs cell-specific expression (e.g. hepatocytes) operably linked to a heterologous gene. Heterologous in this context refers to any nucleotide sequence or gene which is not native to the AAV or B19 parvovirus (e.g. desaturase). Typically the AAV and B19 coding regions have been deleted, resulting in a safe, non-cytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference in its entirety for material related to the AAV vector. In some embodiments, the promoter directs cell-specific expression in the liver. Non-limiting examples include the α1-antitrypsin (AT) promoter, thyroxine binding globulin promoter, human albumin promoter, liver-specific (LSP) promoter consisting of the 475 bp thyroid hormone binding globulin promoter and 2 copies of the 96 bp bikunin/α1-microglobulin enhancer, the DC190 promoter (728 bp) containing a 520 bp human albumin promoter and 2 copies of the 99 bp prothrombin enhancer or the DC172 promoter (1.272 kb) consisting of a 890 bp human (α1-antitrypsin promoter and 2 copies of the 160 bp a α1-microglobulin enhancer. In an exemplary embodiment, the cell-specific promoter is a liver-specific thyroxine binding globulin (TBG) promoter.

As used herein, the term "AAV vector" means a vector derived from an adeno-associated virus serotype. In non-limitation examples AAV vectors include, AAV1, AAV2, AAV3, AAV4, AAV5, AAV6, AAV7, AAV8, AAV9, and mutated forms thereof. AAV vectors can have one or more of the AAV wild-type genes deleted in whole or part, preferably the rep and/or cap genes, but retain functional flanking ITR sequences. Despite the high degree of homology, the different serotypes have tropisms for different tissues. In an exemplary embodiment, the AAV vector is AAV9.

An AAV vector, as disclosed herein, can be generated using any AAV serotype known in the art. Several AAV serotypes and over 100 AAV variants have been isolated from adenovirus stocks or from human or nonhuman primate tissues (reviewed in, e.g., Wu et al., Molecular Therapy, 14(3): 316-327 (2006)). Generally, the AAV serotypes have genomic sequences of significant homology at the nucleic acid sequence and amino acid sequence levels, such that different serotypes have an identical set of genetic functions, produce virions which are essentially physically and functionally equivalent, and replicate and assemble by practically identical mechanisms. AAV serotypes 1-6 and 7-9 are defined as "true" serotypes, in that they do not efficiently cross-react with neutralizing sera specific for all other existing and characterized serotypes. In contrast, AAV serotypes 6, 10 (also referred to as Rh10), and 11 are considered "variant" serotypes as they do not adhere to the definition of a "true" serotype. AAV serotype 2 (AAV2) has been used extensively for gene therapy applications due to its lack of pathogenicity, wide range of infectivity, and ability to establish long-term transgene expression (see, e.g., Carter, B. J., Hum. Gene Ther., 16: 541-550 (2005); and Wu et al., supra). Genome sequences of various AAV serotypes and comparisons thereof are disclosed in, for example, GenBank Accession numbers U89790, J01901, AF043303, and AF085716; Chiorini et al., J. Virol., 71: 6823-33 (1997); Srivastava et al., J. Virol., 45: 555-64 (1983); Chiorini et al., J. Virol., 73: 1309-1319 (1999); Rutledge et al., J. Virol., 72: 309-319 (1998); and Wu et al., J. Virol., 74: 8635-47 (2000)).

AAV rep and ITR sequences are particularly conserved across most AAV serotypes. For example, the Rep78 proteins of AAV2, AAV3A, AAV3B, AAV4, and AAV6 are reportedly about 89-93% identical (see Bantel-Schaal et al., J. Virol., 73(2): 939-947 (1999)). It has been reported that AAV serotypes 2, 3A, 3B, and 6 share about 82% total nucleotide sequence identity at the genome level (Bantel-Schaal et al., supra). Moreover, the rep sequences and ITRs of many AAV serotypes are known to efficiently cross-complement (i.e., functionally substitute) corresponding sequences from other serotypes during production of AAV particles in mammalian cells.

Generally, the cap proteins, which determine the cellular tropicity of the AAV particle, and related cap protein-encoding sequences, are significantly less conserved than Rep genes across different AAV serotypes. In view of the ability Rep and ITR sequences to cross-complement corresponding sequences of other serotypes, the AAV vector can comprise a mixture of serotypes and thereby be a "chimeric" or "pseudotyped" AAV vector. A chimeric AAV vector typically comprises AAV capsid proteins derived from two or more (e.g., 2, 3, 4, etc.) different AAV serotypes. In contrast, a pseudotyped AAV vector comprises one or more ITRs of one AAV serotype packaged into a capsid of another AAV serotype. Chimeric and pseudotyped AAV vectors are further described in, for example, U.S. Pat. No. 6,723,551; Flotte, Mol. Ther., 13(1): 1-2 (2006); Gao et al., J. Virol., 78: 6381-6388 (2004); Gao et al., Proc. Natl. Acad. Sci. USA, 99: 11854-11859 (2002); De et al., Mol. Ther., 13: 67-76 (2006); and Gao et al., Mol. Ther., 13: 77-87 (2006).

In one embodiment, the AAV vector is generated using an AAV that infects humans (e.g., AAV2). Alternatively, the AAV vector is generated using an AAV that infects non-human primates, such as, for example, the great apes (e.g., chimpanzees), Old World monkeys (e.g., macaques), and New World monkeys (e.g., marmosets). Preferably, the AAV vector is generated using an AAV that infects a non-human primate pseudotyped with an AAV that infects humans. Examples of such pseudotyped AAV vectors are disclosed in, e.g., Cearley et al., Molecular Therapy, 13: 528-537 (2006). In one embodiment, an AAV vector can be generated which comprises a capsid protein from an AAV that infects rhesus macaques pseudotyped with AAV2 inverted terminal repeats (ITRs). In a particularly preferred embodiment, the inventive AAV vector comprises a capsid protein from AAV10 (also referred to as "AAVrh.10"), which infects rhesus macaques pseudotyped with AAV2 ITRs (see, e.g., Watanabe et al., Gene Ther., 17(8): 1042-1051 (2010); and Mao et al., Hum. Gene Therapy, 22: 1525-1535 (2011)).

An AAV vector, as disclosed herein, comprises a nucleic acid sequence encoding a desaturase polypeptide. "Nucleic acid sequence" is intended to encompass a polymer of DNA or RNA, i.e., a polynucleotide, which can be single-stranded or double-stranded and which can contain non-natural or altered nucleotides. The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to, methylated and/or capped polynucleotides.

In some embodiments, a vector comprising a nucleic acid sequence encoding a desaturase can be a plasmid, cosmid, yeast artificial chromosome (YAC), bacterial artificial chromosome (BAC), viral vector or bacteriophage. The vectors can provide for replication of desaturase nucleic acids, expression of desaturase polypeptides or integration of desaturase nucleic acids into the chromosome of a host cell. The choice of vector is dependent on the desired purpose. Certain cloning vectors are useful for cloning, mutation and manipulation of the desaturase nucleic acid. Other vectors are useful for expression of the desaturase polypeptide, being able to express the polypeptide in large amounts for purification purposes or to express the desaturase polypeptide in a temporal or tissue specific manner. The vector can also be chosen on the basis of the host cell, e.g., to facilitate expression in bacteria, mammalian cells, insect cells, fish cell (e.g., zebrafish) and/or amphibian cells. The choice of matching vector to host cell is apparent to one of skill in the art, and the types of host cells are discussed below. Many vectors or vector systems are available commercially, for example, the pET bacterial expression system (Invitrogen™, Carlsbad Calif.).

The vectors disclosed herein can be viral or non-viral vectors. For example, as discussed above the disclosed vectors can be viral vectors. There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991). Such methods are well known in the art and readily adaptable for use with the compositions and methods described herein. In certain cases, the methods will be modified to specifically function with large DNA molecules. Further, these methods can be used to target certain neurodegenerative diseases or disorders and cell populations by using the targeting characteristics of the carrier.

Vectors can include various components including, but not limited to, an origin of replication, one or more marker or selectable genes (e.g. GFP, neo), promoters, enhancers, terminators, poly-adenylation sequences, repressors or activators. Such elements are provided in the vector so as to be operably linked to the coding region of the desaturase—encoding nucleic acid, thereby facilitating expression in a host cell of interest. Cloning and expression vectors can contain an origin of replication which allows the vector to replicate in the host cells. Vectors can also include a selectable marker, e.g., to confer a resistance to a drug or compliment complement deficiencies in growth. Examples of drug resistance markers include, but are not limited to, ampicillin, tetracycline, neomycin or methotrexate. Examples of other marker genes can be the fluorescent polypeptides such as one of the members of the fluorescent family of proteins, for example, GFP, YFP, BFP, RFP etc. These markers can be contained on the same vector as the gene of interest or can be on separate vectors and co-transfected with the vector containing the gene of interest.

The vector can contain a promoter that is suitable for expression of the desaturase in mammalian cells, which promoter can be operably linked to provide for inducible or constitutive expression of a desaturase polypeptide. Exemplary inducible promoters include, for example, the metallothionine promoter or an ecdysone-responsive promoter. Exemplary constitutive promoters include, for example, the viral promoters from cytomegalovirus (CMV), Rous Sarcoma virus (RSV), Simian virus 40 (SV40), avian sarcoma virus, the beta-actin promoter and the heat-shock promoters. The promoter can be chosen for its tissue specificity. Certain promoters only express in certain tissues, and when it is desirable to express the polypeptide of interest only in a selected tissue, one of these promoters can be used. The choice of promoter will be apparent to one of skill in the art for the desired host cell system.

The vector encoding a desaturase can be a viral vector. Examples of viral vectors include retroviral vectors, such as: adenovirus, simian virus 40 (SV40), cytomegalovirus (CMV), Moloney murine leukemia virus (MoMuLv), Rous Sarcoma Virus (RSV), lentivirus, herpesvirus, poxvirus and vaccinia virus. A viral vector can be used to facilitate expression in a target cell, e.g., for production of desaturase or for use in therapy (e.g., to deliver a desaturase to a subject by expression from the vector). Where used for therapy, desaturase-encoding vectors (e.g., viral vectors), can be administered directly to the patient via an appropriate route or can be administered using an ex vivo strategy using subject cells (autologous) or allogeneic cells, which are suitable for administration to the patient to be treated.

As used herein, plasmid or viral vectors are agents that transport the disclosed nucleic acids, such as a nucleic acid sequence capable of encoding one or more of the disclosed peptides into the cell without degradation and include a promoter yielding expression of the gene in the cells into which it is delivered. In some embodiments the nucleic acid sequences disclosed herein are derived from any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Lentiviral vectors can carry large payloads and are relatively easy to work with, and can transfect non-dividing cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. The viral vectors may be formulated in pharmaceutical compositions as those described above Retroviral vectors, in general, are described by Verma, I. M., Retroviral vectors for gene transfer. In Microbiology, Amer. Soc. for Microbiology, pp. 229-232, Washington, (1985), which is hereby incorporated by reference in its entirety. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference in their entirety for their teaching of methods for using retroviral vectors for gene therapy.

Other useful systems include, for example, replicating and host-restricted non-replicating vaccinia virus vectors. In addition, the disclosed nucleic acid sequences can be delivered to a target cell in a non-nucleic acid based system. For example, the disclosed polynucleotides can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed expression vectors, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a peptide and a cationic liposome can be administered to the blood, to a target organ, or inhaled into the respiratory tract to target cells of the respiratory tract. For example, a composition comprising a peptide or nucleic acid sequence described herein and a cationic liposome can be administered to a subjects lung cells. Regarding liposomes, see, e.g., Brigham et al. Am. J. Resp. Cell. Mol. Biol. 1:95-100 (1989); Feigner et al. Proc. Natl. Acad. Sci USA 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

Host cells modified to provide for expression of a desaturase peptide disclosed herein are also contemplated. Such host cells can be modified to express a Desaturase polypeptide from either an episomal or genomically integrated nucleic acid. Such host cells can be produced by any suitable method, e.g., electroporation, transfection or transformation with a vector encoding a desaturase polypeptide. Host cells can be selected according to a desired use (e.g., mammalian cell expression), and modified to provide for desaturase expression according to methods well known in the art. Techniques for introducing the vectors into host cells and subsequent culture of the host cells are well known in the art.

Host cells (e.g., mammalian host cells) suitable for replication and expression of desaturase containing vectors are provided, wherein the cells may be stably or transiently transfected and/or stably or transiently express a desaturase. Such desaturase-expressing mammalian cells find use in, for example, production of a desaturase. In addition, mammalian cell lines can be selected for use in replicating, packaging and producing high titers of virus particles which contain a desaturase of interest or nucleic acid-encoding a desaturase. Such desaturase containing viruses can then be used to provide for delivery of desaturase-encoding nucleic acids and desaturase polypeptides to a subject in need thereof.

Exemplary host cells include bacteria, yeast, mammalian cells (e.g., human cells or cell lines), insect cells, and the like. Examples of bacterial host cells include *E. coli* and other bacteria which can find use in cloning, manipulation and production of desaturase nucleic acids or the production of desaturase polypeptide. Examples of mammalian cells include, but are not limited to, Chinese hamster ovary (CHO) cells, HEK 293 cells, human cervical carcinoma cells (Hela), canine kidney cells (MDCK), human liver cells (HepG2), baby hamster kidney cells (BHK), and monkey kidney cells (CV1).

The nucleic acid molecules described herein and the proteins they encode can be included in pharmaceutical compositions. For example, the compositions can include an expression vector described herein and a physiologically acceptable diluent (e.g., normal saline or a physiologically acceptable buffer, such as phosphate-buffered saline). The nucleic acid molecule may be present in a concentrated form or in an amount suitable for administration to a subject (e.g., a therapeutically effective amount). The amount administered would be considered therapeutically effective when, upon administration to a subject, the nucleic acid expresses an n-3 desaturase to an extent that the cellular n-3 PUFA content and/or tissue n-3 PUFA content and/or serum n-3 PUFA content in the subject is elevated and/or the ratio of n-6:n-3 PUFAs is more favorably balanced.

RNA analysis and enzymatic assays can be performed to assess desaturase gene expression, and gas chromatography-mass spectrometry can be used to determine fatty acid profiles (these are standard techniques that one of ordinary skill in the art could use to assess any variant of the desaturase sequence for biological activity; or incorporate in any method of assessing a sample obtained from a subject such as a human patient or non-human mammals for fat-1 expression).

The disclosure also encompasses non-human animals (e.g., a mammal, a bird, or a fish) that include a nucleic acid molecule described herein or have been given a probiotic composition as described herein. The animals may be those that are kept, bred, caught, or hunted for food (e.g., consumption by humans or other animals (e.g., livestock or pets). As noted, the mammal can be a mouse, a rat, a goat, a cow, a pig, a rabbit, a horse, or a sheep; the bird can be a chicken, a turkey, a duck, a goose, or a game hen; and the fish can be a salmon, trout, or tuna.

b) Probiotic Microorganism

In one aspect, the present disclosure is directed to a probiotic microorganism.

The term "microorganism" is used herein in its art recognized meaning and refers in particular to organisms selected from bacteria, archaea, unicellular fungi like e.g. yeast, algae and unicellular protozoa. Preferably, the term "microorganism" is used to denote bacteria and unicellular yeast.

For the purpose of the present disclosure, the term "probiotic" refers to a microorganism capable of exerting a beneficial effect upon administration to a suitable subject or host. Upon proper administration, a probiotic microorganism is capable to survive in said subject or host for a considerable period of time. In particular, the probiotic microorganism of the invention refers to a vital microorganism which, upon proper administration to said subject or host, is capable of proliferation and/or colonization within said subject or host. The present disclosure is not particularly limited with regards to the probiotic microorganism as the skilled person is well aware of microorganisms that can be used as probiotics in the sense of the present disclosure.

There is also ample literature available describing probiotic microorganisms used for treatment of numerous diseases like e.g. inflammatory diseases. In some embodiments, the probiotic microorganism of the disclosure is a microorganism selected from the bacterial genus *lactobacillus, bifidobacterium, escherichia bacteroides, clostridium, lactococcus* and/or *streptococcus*. In some embodiments, the probiotic of the disclosure is selected from the yeast genus *saccharomyces*. Thus, the probiotic microorganism of the invention may be selected from *Bifidobacterium longum, Bifidobacterium breve, Bifidobacterium bifidum, Bifidobacterium infantis, Bifidobacterium animalis (Bifidobacterium lactis), Bifidobacterium animalis (Bifidobacterium lactis)* strain Bb 12, *Lactobacillus acidophilus, Lactobacillus acidophilus* strain La5, *Lactobacillus casei, Lactobacillus johnsonii, Lactobacillus johnsonii* strain LA1, *Lactobacillus raffinolactis, Lactobacillus lactis, Lactobacillus salivarius, Lactobacillus plantarum, Lactobacillus paracasei, Lactobacillus bulgaricus, Lactobacillus rhamnosus, Lactobacillus rhamnosus* strain GG, *Escherichia coli, Escherichia coli* strain Nissle, *Escherichia coli* strain Nissle 1917 (EcN), *Enterococcus durans, Faecalibacterium prausnitzii, Pediococcus pentoseceus, Saccharomyces thermophilus* and/or *Saccharomyces boulardii.*

According to the present disclosure the probiotic microorganism is genetically engineered to express a desaturase according to the disclosure. Suitable desaturase nucleic acids and peptides are discussed supra in section I(a).

In some embodiments, the probiotic microorganism of the disclosure may comprise or consist of: an amino acid sequence with SEQ ID NO: 2; and/or an amino acid sequence that is at least 70% identical, preferably at least 80% identical, more preferably at least 90% identical and most preferably at least 99% identical to an amino acid sequence with SEQ ID NO:2.

An engineered probiotic microorganism may be stably or transiently transformed or transfected to express the desired desaturase.

The present disclosure is also directed to a pharmaceutical composition comprising a transgenic probiotic microorganism of the invention and at least one pharmaceutically acceptable excipient. In other embodiment, the food supplements or food products comprising a transgenic probiotic microorganism of the present disclosure. Alternatively, the engineered probiotic microorganism or the pharmaceutical composition of the invention may be provided in encapsulated form, may be used as food supplement or may be incorporated into food products.

In addition to ingestion, probiotic may be applied to epithelial (e.g., oral cavity) or mucosal tissues (e.g., vaginal canal) in a topical manner to modify the microbiome in these regions.

c) Components of the Composition

The present disclosure also provides pharmaceutical compositions. The pharmaceutical composition comprises a desaturase as disclosed herein, as an active agent, and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

(i) Diluent

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

(ii) Binder

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

(iii) Filler

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

(iv) Buffering Agent

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

(v) pH Modifier

In various embodiments, the excipient may be a pH modifier. By way of non-limiting example, the pH modifying agent may be sodium carbonate, sodium bicarbonate, sodium citrate, citric acid, or phosphoric acid.

(vi) Disintegrant

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

(vii) Dispersant

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

(viii) Excipient

In another alternate embodiment, the excipient may be a preservative. Non-limiting examples of suitable preserva-tives include antioxidants, such as BHA, BHT, vitamin A, vitamin C, vitamin E, or retinyl palm itate, citric acid, sodium citrate; chelators such as EDTA or EGTA; and antimicrobials, such as parabens, chlorobutanol, or phenol.

(ix) Lubricant

In a further embodiment, the excipient may be a lubricant. Non-limiting examples of suitable lubricants include minerals such as talc or silica; and fats such as vegetable stearin, magnesium stearate, or stearic acid.

(x) Taste-Masking Agent

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

(xi) Flavoring Agent

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

(xii) Coloring Agent

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Maryland, 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

(d) Administration (i) Dosage Forms

The composition can be formulated into various dosage forms and administered by a number of different means that will deliver a therapeutically effective amount of the active ingredient. Such compositions can be administered orally (e.g. inhalation), parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, intra-articular, or intrasternal injection, or infusion techniques. Formulation of drugs is discussed in, for example, Gennaro, A. R., Remington's Pharmaceutical Sciences, Mack Publishing Co., Easton, Pa. (18th ed, 1995), and Liberman, H. A. and Lachman, L., Eds., Pharmaceutical Dosage Forms, Marcel Dekker Inc., New York, N.Y. (1980). In a specific embodiment, a composition may be a food supplement or a composition may be a cosmetic.

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof. For administration by inhalation, the compounds are delivered in the form of an aerosol spray from pressured container or dispenser which contains a suitable propellant, e.g., a gas such as carbon dioxide, or a nebulizer.

For parenteral administration (including cutaneous, subcutaneous, intraocular, intradermal, intravenous, intramuscular, intra-articular and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules, and tablets.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols, or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles, and mouth washes. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising the desaturase nucleic acids or probiotic, is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present disclosure. Non-limiting examples of suitable structured fluid delivery systems may include nanoparticles, liposomes, microemulsions, micelles, dendrimers, and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of the desaturase, in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, the composition comprising the desaturase may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palm itate), n-octadecanoate (stearate), n-eicosanoate (arachidate), n-docosanoate (behenate), n-tetracosanoate (lignocerate), cis-9-hexadecenoate (palm itoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palm itoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3, 3, 3',3'-tetramethylindo carbocyanine methanesulfonate, N-4-(delinoleylaminostyryl)-N- methylpyridinium iodide, or 1,1, -dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying the one or more of a tricyclic antipsychotic, vasodilator, antibiotic/antiseptic, aryl piperazine or derivatives thereof, may be prepared by any known method of preparing liposomes for drug delivery, such as, for example, detailed in U.S. Pat. Nos. 4,241,046; 4,394,448; 4,529,561; 4,755,388; 4,828,837; 4,925,661; 4,954,345; 4,957,735; 5,043,164; 5,064,655; 5,077,211; and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of one or more of a proteotoxicity reducing agent or derivatives thereof, concentration and composition of lipid, concentration of multivalent cations, rate of mixing, presence of and concentration of solvent.

In another embodiment, a composition of the disclosure may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the disclosure generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. The one or more of a tricyclic antipsychotic, vasodilator, antibiotic/antiseptic, aryl piperazine or derivatives thereof may be encapsulated in a microemulsion by any method generally known in the art.

In yet another embodiment, the nucleic acids encoding a desaturase, may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the disclosure therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the disclosure. Generally, the size of dendrimers may range from about 1 nm to about 100 nm.

Generally, a safe and effective amount of a composition comprising a desaturase is, for example, that amount that would cause the desired effect in a subject while minimizing undesired side effects. In various embodiments, an effective amount of a composition comprising a desaturase described herein can substantially increase omega-3 levels, reduce the omega 6:omega 3 ratio, reduce systemic or local inflammation, reduce osteoarthritis severity, reduce adiposity, reduce body mass, improve bone microstructure, increase the number of anti-inflammatory macrophages, or prevent premature cell senescence in a subject.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The present disclosure encompasses pharmaceutical compositions comprising a desaturase as disclosed above, so as to facilitate administration and promote stability of the active agent. For example, a compound of this disclosure may be admixed with at least one pharmaceutically acceptable carrier or excipient resulting in a pharmaceutical composition which is capably and effectively administered (given) to a living subject, such as to a suitable subject (i.e.

"a subject in need of treatment" or "a subject in need thereof"). For the purposes of the aspects and embodiments of the disclosure, the subject may be a human or any other animal.

The present disclosure describes polypeptides, peptides, and proteins for use in various embodiments of the present disclosure. For example, specific polypeptides are assayed for their abilities to convert omega 6 to omega 3. In specific embodiments, all or part of the proteins of the disclosure can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Alternatively, recombinant DNA technology may be employed wherein a nucleotide sequence which encodes a peptide of the disclosure is inserted into an expression vector, transformed or transfected into an appropriate host cell and cultivated under conditions suitable for expression.

A number of selection systems may be used including, but not limited to HSV thymidine kinase, hypoxanthine-guanine phosphoribosyltransferase, and adenine phosphoribosyltransferase genes, in tk-, hgprt- or aprt-cells, respectively. Also, anti-metabolite resistance can be used as the basis of selection: dhfr, which confers resistance to trimethoprim and methotrexate; gpt, which confers resistance to mycophenolic acid; neo, which confers resistance to the aminoglycoside G418; and hygro, which confers resistance to hygromycin.

Animal cells can be propagated in vitro in two modes: as non-anchorage-dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent cells.

The compositions and related methods of the present disclosure, particularly administration of a composition comprising a desaturase to a patient/subject, may also be used in combination with the administration of traditional therapies for inflammation, obesity, or osteoarthritis.

Various combinations may be employed, for example anti-inflammatory therapy is "A" and desaturase composition, is "B": A/B/A B/NB B/B/A A/A/B A/B/B B/A/A A/B/B/B B/NB/B B/B/B/A B/B/NB A/A/B/B A/B/NB A/B/ B/A B/B/A/A B/A/B/A B/A/A/B A/A/A/B B/A/A/A A/B/ A/A A/A/B/A.

In some embodiments, pharmaceutical compositions are administered to a subject. Different aspects of the present disclosure involve administering an effective amount of a composition to a subject. In some embodiments of the present disclosure, a composition comprising a desaturase may be administered to the subject such as a patient to increase omega-3 levels, reduce the omega 6:omega 3 ratio, reduce systemic inflammation, reduce osteoarthritis severity, reduce adiposity, reduce body mass, improve bone microstructure, increase the number of anti-inflammatory macrophages, or prevent premature cell senescence.

The active compositions of the present disclosure can be formulated for parenteral administration, e.g., formulated for injection via the intravenous, intramuscular, sub-cutaneous, or even intraperitoneal routes. The preparation of an aqueous composition that contains a composition or compositions of the present disclosure will be known to those of skill in the art in light of the present disclosure. Typically, such compositions can be prepared as injectables, either as liquid solutions or suspensions; solid forms suitable for use to prepare solutions or suspensions upon the addition of a liquid prior to injection can also be prepared; and, the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the protection desired.

Additional formulations of pharmaceutical delivery systems may be in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980). Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners. A suitable pharmaceutically acceptable carrier to maintain optimum stability, shelf-life, efficacy, and function of the delivery system would be apparent to one of ordinary skill in the art.

Controlled-release (or sustained-release) preparations may be formulated to extend the activity of the agent(s) reduce the dosage frequency. Controlled-release preparations can also be used to affect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

II. Methods

It is well accepted that a high-fat diet can lead to obesity and a number of related metabolic disorders that are associated with detrimental changes in the musculoskeletal system, the reproductive system, the cardiovascular system, and many other physiologic functions. The present disclosure has shown that the dietary content plays a critical role in the process. For example, diets rich in omega-6 fatty acids are detrimental, whereas dietary supplementation with omega-3 reverses or reduces these effects. Furthermore, transgenic animals harboring the fat-1 gene, show amelioration of the detrimental omega-6 effects.

The fat-1 gene (expressed naturally in Caenorhabditis elegans) encodes an omega-3 fatty acid desaturase which converts omega-6 to omega-3 fatty acids. Humans and other mammals lack the fat-1 gene and cannot synthesize omega-6 and omega-3 fatty acids. Therefore the body's composition of these fatty acids is entirely dependent on dietary intake. An elevated omega-6:omega-3 ratio is typical of Western diets and has been reported to be pro-inflammatory, while a lower ratio is anti-inflammatory and associated with reductions in disease incidences and progression.

Thus the present disclosure provides methods for increasing omega-3 fatty acid levels in a subject, the methods generally comprise administering to the subject a composition comprising nucleic acids encoding an n-3 desaturase, such as fat-1. In another embodiment, the present disclosure provides methods for reducing the level of omega-6 fatty acids in a subject, the methods generally comprise administering to the subject a composition comprising nucleic acids encoding an n-3 desaturase. In still another embodiment, the present disclosure provides methods to reduce the omega-6 to omega-3 ratio in a subject, the methods generally comprising administering to the subject a composition comprising nucleic acids encoding an n-3 desaturase. Thus, the present disclosure provides methods for treating subjects (including humans and other mammals) who have, or who may develop, a condition associated with an insufficiency of n-3 PUFA or an imbalance in the ratio of n-3:n-6 PUFAs by administering a nucleic acid encoding an n-3 desaturase or a biologically active variant thereof (e.g., a fragment, mutant, or codon optimized sequence). Alternatively, one can administer the protein encoded by the nucleic acid or biologically active variant or a probiotic compositions where the probiotic microorganism expresses a n-3 desaturase. The treatment methods can be applied to subjects who have joint disease (e.g., osteoarthritis or post-traumatic arthritis), an arrhythmia or cardiovascular disease (as evidenced, for example, by high plasma triglyceride levels or hypertension), cancer (e.g., breast cancer or colon cancer), inflammatory or autoimmune diseases (such as rheumatoid arthritis, multiple sclerosis, inflammatory bowel disease (IBD), asthma, chronic obstructive pulmonary disease, lupus, diabetes, Sjogren's syndrome transplantation, ankylosing spondylitis, polyarteritis nodosa, reiter's syndrome, or scleroderma), or a malformation (or threatened malformation, as occurs in premature infants) of the retina or brain. Suitable subjects also include those having or diagnosed as having diabetes, obesity, a skin disorder, renal disease, ulcerative colitis, or Crohn's disease. Expression of fat-1 can inhibit premature cellular senescence in cells, and thus the methods of the disclosure can also be used to treat or prevent diseases or disorders associated with cellular senescence. In each of the preceding embodiments, suitable compositions and n-3 desaturases are discussed above in section I.

In another aspect, the present disclosure provides a method of reducing systemic metabolic inflammation in a subject by administering to the subject a composition comprising a nucleic acid encoding an n-3 desaturase. In one embodiment, reduced systemic metabolic inflammation is measure by a reduction in inflammatory cytokines, such as, IL-1β, IL-1α, TNFα, or IL-6, relative to an untreated subject. In another aspect, administering subject a composition comprising a nucleic acid encoding an n-3 desaturase increases the percentage of anti-inflammatory cells (e.g., M2-like macrophages).

In yet another aspect, the present disclosure provides methods for treating osteoarthritis. In some embodiments, the osteoarthritis is associated with obesity in the subject. In some embodiments, administering to the subject a composition comprising a nucleic acid encoding an n-3 desaturase results in improved bone microstructure. In some embodiments, administering to the subject a composition comprising a nucleic acid encoding an n-3 desaturase reduces adiposity and/or body mass in the subject. In some embodiments, administering to the subject a composition comprising a nucleic acid encoding an n-3 desaturase increases wound healing in the subject. In some embodiments, administering to the subject a composition comprising a nucleic acid encoding an n-3 desaturase reduces systemic or local inflammation in the subject.

In still yet another aspect, the present disclosure provides methods for reducing obesity-induced cell senescence in a subject. In some embodiments, the subject administered a composition comprising a nucleic acid encoding an n-3 desaturase has decreased content of β-gal positive cells and/or decreased expression of p21 protein and/or reduced p16INK14a expressing cells. In some embodiments, reduced cellular senescence occurs in tissues such as adipose tissue, muscle tissue, and/or cartilage. As described herein, a high-fat obesogenic diet causes premature cell senescence in both AT and cartilage, while fat-1 gene therapy mitigates this process.

In each of the above embodiments, the use viral vectors, such as adeno-associated virus (AAV) can be used to deliver the n-3 desaturase, such as the fat-1 gene to any animal or human. This overcomes the need to create a transgenic line. For animals, this can provide health benefits for companion animals but also allows development of livestock animals with increased health omega-3 fatty acid content.

In each of the above embodiments, an alternative approach can be to deliver the n-3 desaturase gene via an engineered microorganism, such as a bacteria in the gut microbiome.

This disclosure provides a safe and simple means for expression of the n-3 desaturase (e.g., fat-1 gene) within the mammalian gut without direct genome editing of the receiving subject. This is accomplished by synthetically developing "probiotic" bacteria strains expressing the n-3 desaturase. Non-pathogenic bacteria are transformed with nucleic acids coding for at least the n-3 desaturase gene to generate synthetic probiotics. The synthetic probiotic may be administered orally, promoting their colonization and expansion within the host's microbiome. The synthetic probiotics will provide a means for n-3 desaturase expression within tissue-resident microbiota of mammals.

As noted above, the disclosure also encompasses non-human animals (e.g., a mammal, a bird, or a fish) that include a nucleic acid molecule described herein or have been given a probiotic composition as described herein. The animals may be those that are kept, bred, caught, or hunted for food (e.g., consumption by humans or other animals (e.g., livestock or pets). As noted, the mammal can be a cow, a pig, or a sheep; the bird can be a chicken, a turkey, a duck, a goose, or a game hen; and the fish can be a salmon, trout, or tuna.

Food products or dietary supplements that include these non-human animals or a tissue or processed part thereof are also within the scope of the present disclosure. The products may be unprocessed (as in the case of whole animals, or whole parts of animals (e.g., joints, knuckles, or organs)) or processed from a slaughtered animal or a part thereof (e.g., the bones, fat, skin, or oils obtained therefrom). Methods of making dietary supplements (e.g., fish-oil capsules) are known in the art and can be applied to the use of any of the modified animals of the present disclosure. The disclosure also encompasses methods of making food products or dietary supplements from an animal described herein (e.g., a transgenic mammal, bird or fish). These methods can be carried out in any manner, including any currently known process; it is just that the source is, or includes, a non-human animal (or a part thereof), generated as described herein.

Other methods of the disclosure include improving the content of n-3 fatty acids in a subject's diet by administering to the subject the food product(s) or dietary supplement(s) described above. Alternatively, methods of the disclosure include improving the content of n-3 fatty acids in a subject by providing a probiotic composition comprising an engineered microorganism expressing an n-3 desaturase.

Administration of a composition comprising a nucleic acid encoding an n-3 desaturase can occur as a single event or over a time course of treatment. For example, one or more of a Desaturase can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more. Compositions may be administered 1, 2, 3, 4, 5, 6, 7, 8, 9, 10, 11, 12, 13, 14, 15, 16, 17, 18, 19, 20 or more times, and/or they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months, or any range or combination derivable therein.

RNA analysis and enzymatic assays can be performed to assess desaturase gene expression, and gas chromatography-mass spectrometry can be used to determine fatty acid profiles (these are standard techniques that one of ordinary skill in the art could use to assess any variant of the desaturase sequence for biological activity; or incorporate in any method of assessing a sample obtained from a patient for fat-1 expression).

Methods described herein are generally performed on a subject in need thereof. A subject in need of the therapeutic methods described herein can be a subject having, diagnosed with, suspected of having, or at risk for developing a disease, disorder, or condition as described herein. A determination of the need for treatment will typically be assessed by a history, physical exam, or diagnostic tests consistent with the disease or condition at issue. Diagnosis of the various conditions treatable by the methods described herein is within the skill of the art. The subject can be an animal subject, including a mammal, such as rabbits, horses, cows, dogs, cats, sheep, pigs, mice, rats, monkeys, hamsters, guinea pigs, and humans or chickens. For example, the subject can be a human subject. In some embodiments, a subject of the disclosure is a normal healthy subject. In another aspect, a subject of the disclosure is an obese subject. Obesity is a complex disease involving an excessive amount of body fat. Obesity occurs when a person's body mass index is 30 or greater. In another aspect, a subject of the disclosure has metabolic syndrome.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

As various changes could be made in the above-described materials and methods without departing from the scope of the disclosure, it is intended that all matter contained in the above description and in the examples given below, shall be interpreted as illustrative and not in a limiting sense.

EXAMPLES

The following examples are included to demonstrate various embodiments of the present disclosure. It should be appreciated by those of skill in the art that the techniques disclosed in the examples that follow represent techniques discovered by the inventors to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Figure 1B:
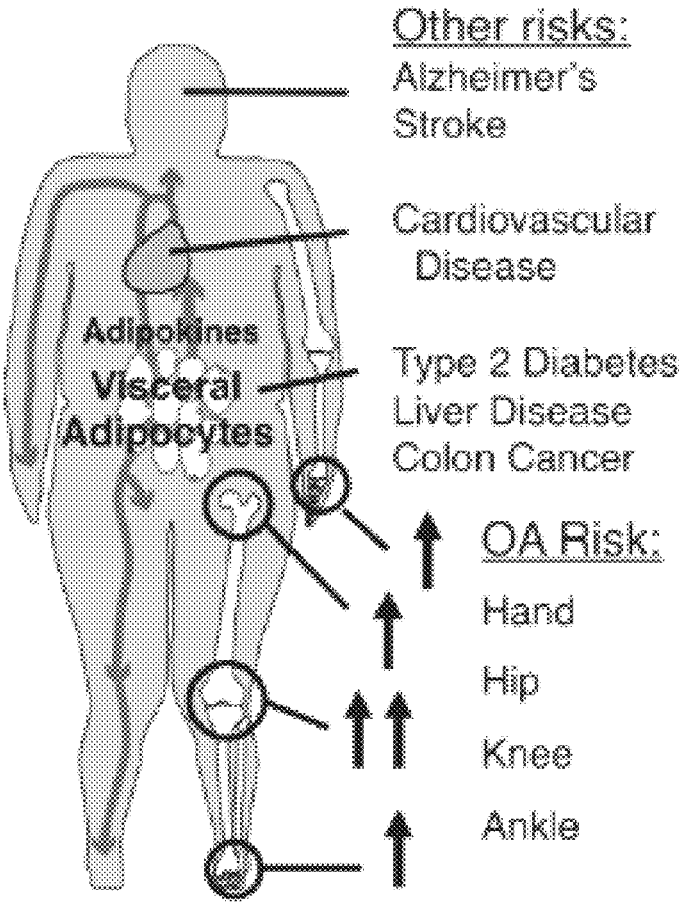
FIG. 1B is a cartoon showing increased osteoarthritis risk with obesity likely involves complex interactions of local and systemic biomechanical factors and inflammation.

Example 1: Gene Therapy for Fat-1 Prevents Systemic Metabolic Inflammation and Post-Traumatic Osteoarthritis in High w-6 Fat-Diet-Induced Obese Mice Fatty acids and their lipid metabolites are increasingly being recognized as potent regulators of the innate immune system (Hotamisligil, G S, Nature, 44:860-7, 2006). Recent findings implicate both the chronic elevation of circulating free fatty acids, as well as the composition of ingested dietary fatty acids, as important mediators of the pro-inflammatory state associated with obesity. Growing evidence indicates that intracellular accumulation and metabolism of free fatty acids trigger inflammatory responses via interactions with nuclear receptors (e.g., PPARs) and kinases (e.g., PKC, IKK, and JNK). Furthermore, free fatty acids can induce TNF-$\alpha$ and IL-6 production by adipocytes and macrophages by activating toll-like receptor 4 via the NF-KB pathway. Saturated fatty acids potently stimulate cytokines in a dose-dependent manner, while trans fatty acids, arachidonic acid, and oleic acid can act as stimulants of cytokine production. Omega-3 polyunsaturated fatty acids (PUFAs), however, did not stimulate cytokine expression and completely inhibited TNF-$\alpha$ expression induced by saturated fatty acid. Although the specific mechanism for this response is unknown, $\omega$-3 PUFAs are well-known for their anti-inflammatory properties. The relative ratio of $\omega$-6:$\omega$-3 fatty acids in the diet have also been implicated in mediating inflammation, as eicosanoids derived from the $\omega$-6 fatty acid, arachidonic acid, e.g., PGE2 and LTB4, are pro-inflammatory (FIG. 1). Western diets are high in $\omega$-6 PUFAs with ratios that are 10-20-fold greater than those found in other parts of the world, which are presumably are characteristic of diets during much of human evolution. Recent in vivo findings support an anti-inflammatory effect of balancing $\omega$-6:$\omega$-3 ratios. Dietary fatty acid content plays a major role in osteoarthritis. In addition, dietary fatty acid content plays a role in wound healing, whereas omega 3 fatty acids promote regeneration.

The risk for developing osteoarthritis (OA), a painful and debilitating multifactorial disease, is 5-fold higher in obese individuals compared to those of normal weight'. Studies have demonstrated that dietary fatty acid (FA) composition, in particular, the omega-6 to omega-3 ratio ($\omega$-6:$\omega$-3), plays a critical role in the development of post-traumatic osteoarthritis (PTA). The FAT-1 enzyme, a non-mammalian FA desaturase that converts $\omega$-6 FAs to $\omega$-3 FAs, provides a useful tool for endogenous reduction of $\omega$-6:$\omega$-3 FAs in the body. Systemic delivery of AAV-mediated fat-1 abrogates joint degeneration and inflammation following destabilization of the medial meniscus (DMM) in mice fed an $\omega$-6-rich high-fat diet.

Methods

Mice. All animal procedures were approved by the IACUC. Five-week-old male C57BL/6 mice were fed either Control (10% fat by kcal, #D11120103) or high-fat diet (HFD) (60% fat by kcal, high in $\omega$-6 Fat, Research Diets

Figures 2A, 2B:
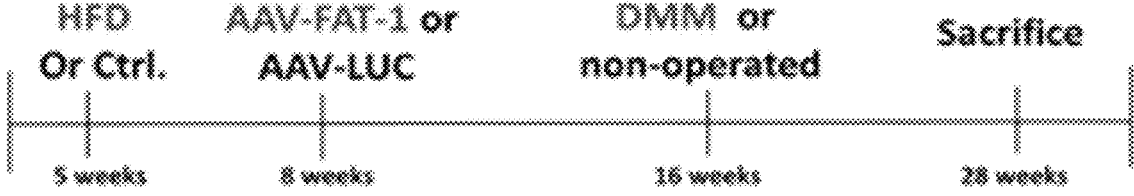
FIG. 2A-2E show the gene delivery of Fat-1 and its effects on HFD mediated osteoarthritis.

D11120105, n=15/dietary group). At 8-weeks of age, either an AAV8-mediated fat-1 or luciferase control gene vectors, both driven by CMV promoter, were delivered via tail vein at a dose of $5\times10^{11}$ vg/mouse (FIG. 2A). At 16-weeks of age, mice received DMM surgery on the left hindlimb to induce knee OA (FIG. 2B). At 12 weeks post-surgery, mice were sacrificed and weighed. Sera were analyzed using a 31-plex Luminex® assay (Eve Technology), OA and synovitis severity were determined histologically, bone changes were measured using microCT (Bruker Skyscan 1176), and epididymal adipose tissue was collected for flow cytometry testing for pro-inflammatory ($CD45^+CD11b^+CD11c^+$) (M1-like) and pro-resolving ($CD45^+CD11b^+CD206^+$ or $CD45^+CD11b^+CD301^+$) (M2-like) macrophages. Statistical analysis was performed using two-way ANOVA within dietary group ($\alpha$=0.05).

Results

Figure 2C:
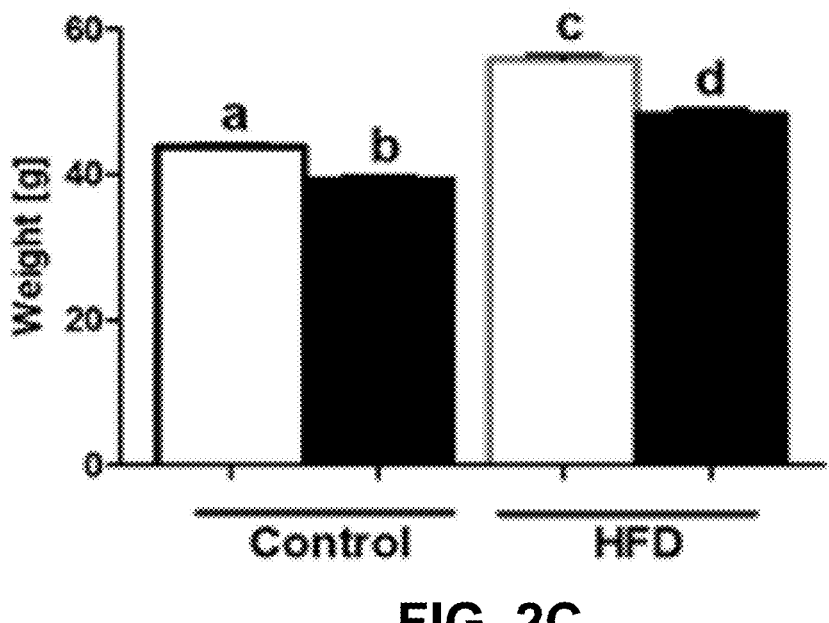
Figure 2D:
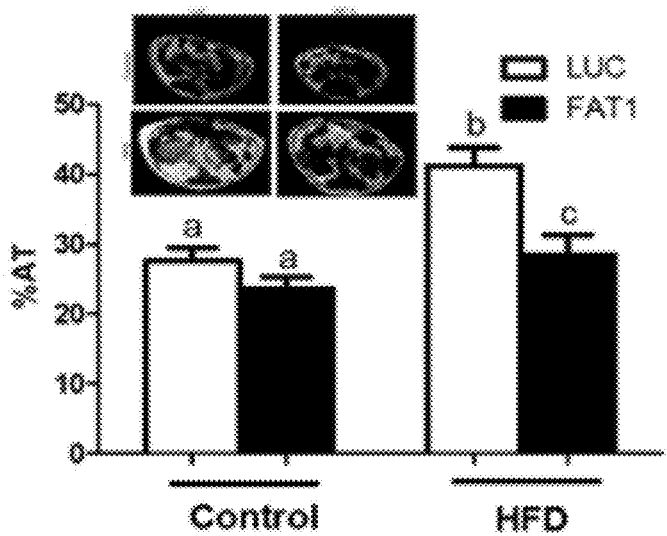
Figure 2E:
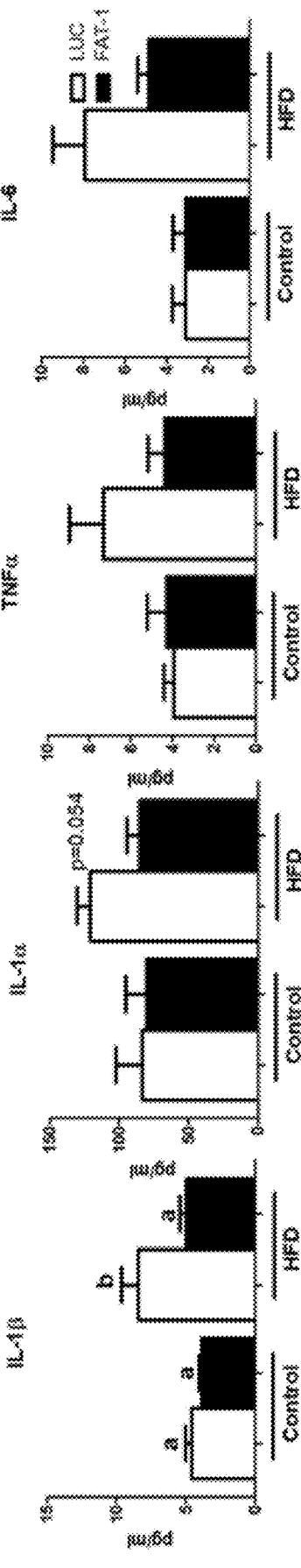
Figure 3A:
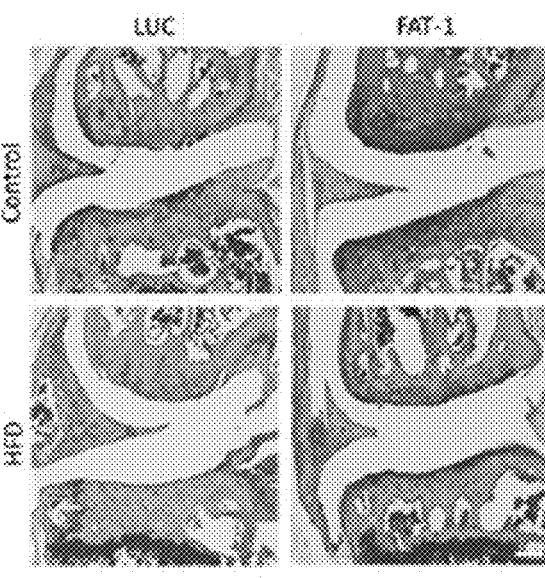
FIG. 3A-3F show Fat-1 overexpression significantly mitigated OA severity in both control and HFD groups.
Figure 3B:
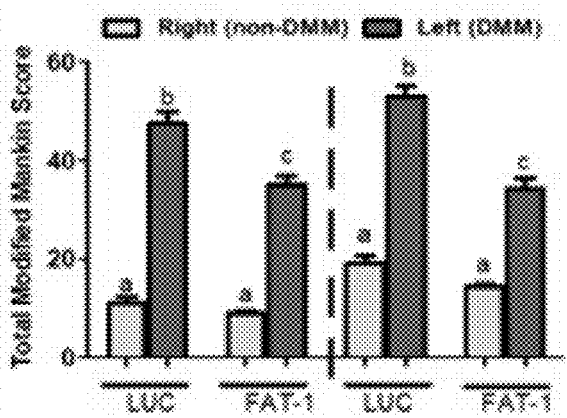
Figure 3C:
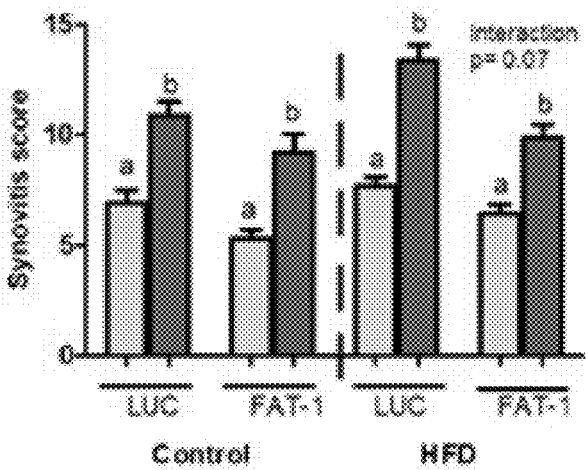
Figure 3D:
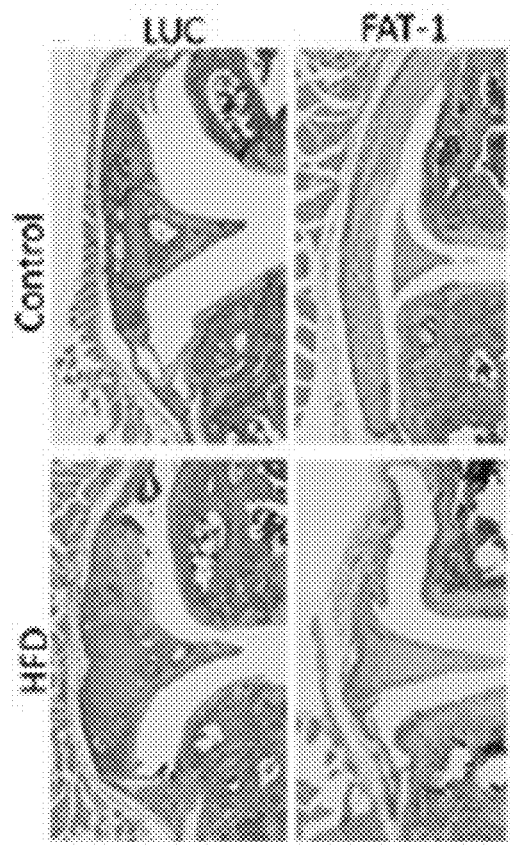
Figure 3E:
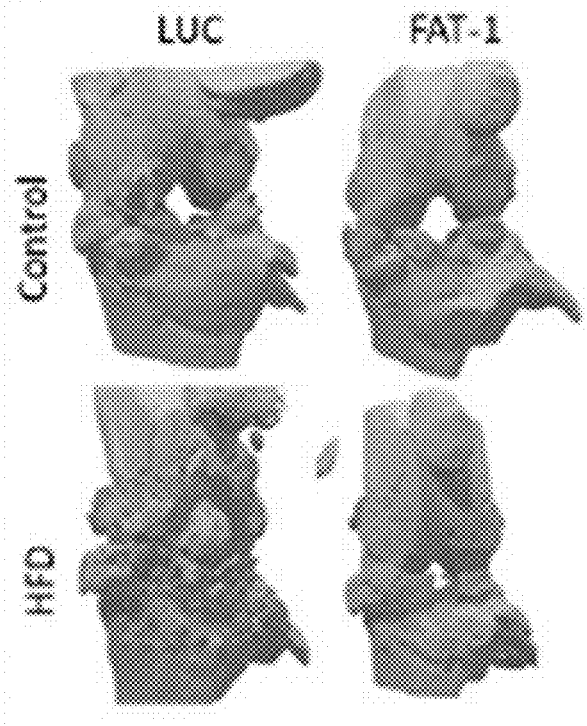
Figure 3F:
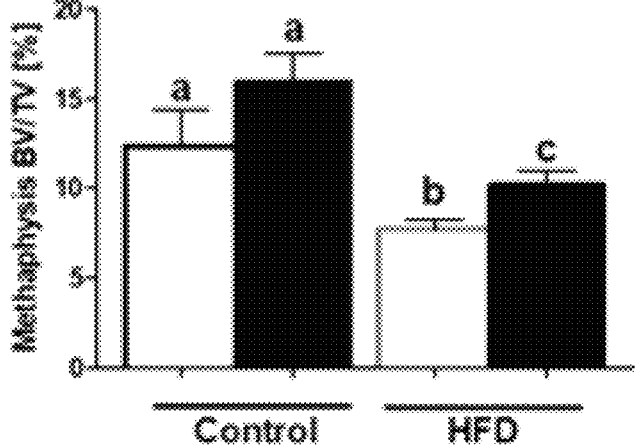
Figure 3F:
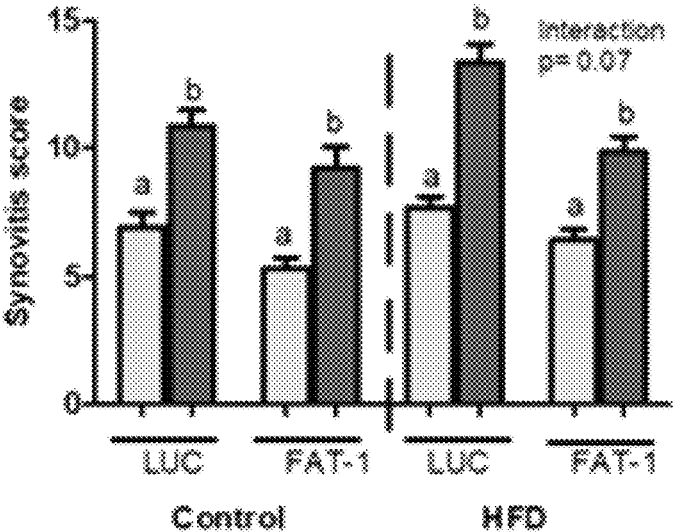
Figure 4A:
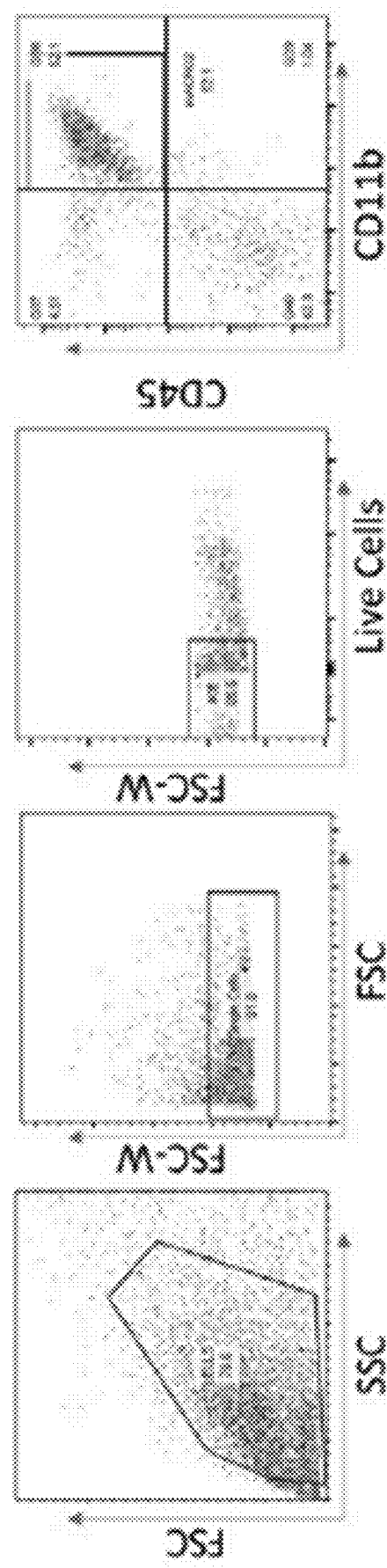
FIG. 4A-4D shows elevated M2-like macrophages levels in epididymal adipose tissue of HFD-FAT1 compared to HFD-LUC mice.
Figure 4B:
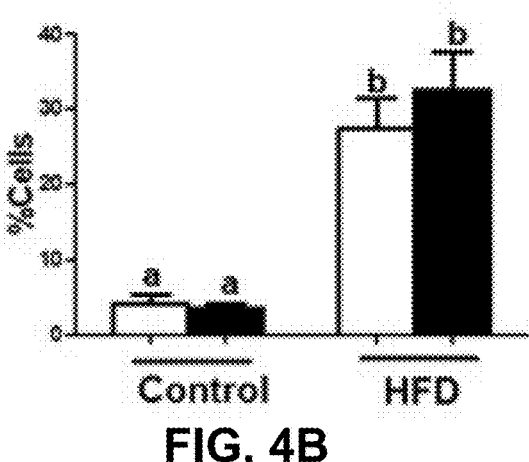
Figure 4C:
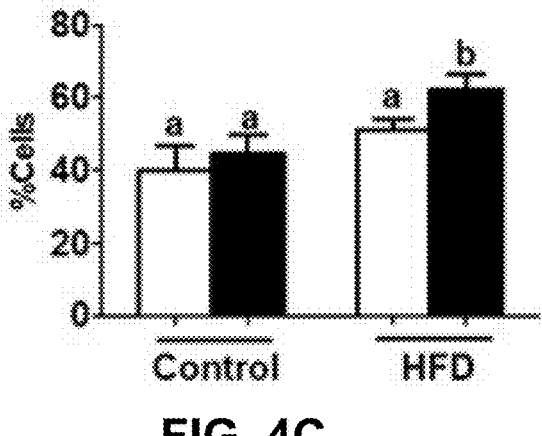
Figure 4D:
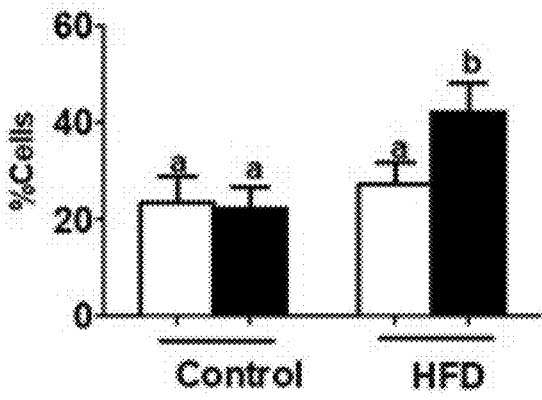

AAV8-mediated overexpression of Fat-1 significantly decreased body weight in both Control and HFD-fed mice (FIG. 2C). There was significantly lower adipose tissue percentage in HFD-fed mice with an AAV-fat-1 compared to HFD overexpressing Luciferase (HFD-LUC and HFD-FAT1 respectively), while there was no change in adiposity in Control mice (Control LUC and Control FAT-1 respectively) (FIG. 2D). Serum IL-1β was significantly reduced, and IL-1α and other pro-inflammatory cytokines such as TNFα and IL-6 trended lower in HFD-FAT1 compared to HFD-LUC mice (FIG. 2E). It was found that Fat-1 overexpression significantly mitigated OA severity in both Control and HFD groups (FIG. 3A, 3B). There was a trend towards lower synovitis score observed in HFD-FAT1 mice compared to HFD-LUC (FIG. 3C, 3D). It was also found that Fat-1 overexpression protected knee joint bone microstructure (FIG. 3E). There was decreased presence of heterotopic ossification in the knee joint and an increased BV/TV, and Tb.N in tibial metaphysis in DMM operated joints of HFD FAT1 mice compared to HFD LUC (FIG. 3F). Flow cytometry analysis (FIG. 4A) did not reveal differences in M1-like macrophages (FIG. 4B); however, there was a significantly higher percentage of M2-like macrophages in epididymal adipose tissue of HFD-FAT1 compared to HFD-LUC (FIG. 4C, 4D).

Although the specific mechanisms by which FAs influence joint health are not fully understood, the imbalance in dietary FA has become an emerging issue in many diseases including OA. These results showed that gene therapy for the FA-desaturase, Fat-1, reduces systemic metabolic inflammation and significantly reduces the severity of PTA. Furthermore, Fat-1 gene delivery had a significant beneficial effect in reducing adiposity and body mass, increasing bone microstructure parameters, and decreasing metabolic inflammation. These findings are consistent with work showing that dietary supplementation with ω-3 FAs can reduce the severity of PTA, potentially due to the anti-inflammatory effects of ω-3. Furthermore, the enrichment in endogenous ω-3 fatty acids in Fat-1 transgenic mice fed HFD was also found to inhibit PTA. However, recent studies have showed that transgenic Fat-1 mice and WT littermates exhibited comparable idiopathic OA scores when fed a lean diet (10% kcal from fat) rich in ω-6 FAs. The present findings suggest several potential mechanisms for these effects downstream of decreased ω-6:ω-3 ratios observed in Fat-1 overexpressing mice, including the reduction of inflammatory cytokines such as IL-1α and an increase in M2-like macrophages in epididymal adipose tissue.

By reducing the ω-6:ω-3 FA ratio, Fat-1 gene therapy prevented obesity-associated metabolic inflammation and mitigated the severity of PTA, potentially provide a therapeutic approach for treating OA.

Example 2: Gene Therapy for Fat-1 Prevents Obesity-Induced Cell Senescence Associated with Osteoarthritis in Mice Osteoarthritis (OA) is a multifactorial disease affecting all tissues within the joint and is highly associated with obesity. Dietary fatty acid (FA) composition, in particular, the omega-6 to omega-3 FA ratio (ω-6:ω-3), plays a critical role in the development of post-traumatic osteoarthritis (PTOA) with obesity. Example 1 has shown that gene therapy for overexpression of Fat-1, an ω-3 FA desaturase that can convert ω-6 FAs into ω-3 FAs, significantly reduces systemic metabolic inflammation as well as the severity of PTOA in mice. Furthermore, Fat-1 gene delivery had a significant beneficial effect in reducing adiposity and body mass and improving bone microstructure parameters. However, the precise mechanism by which the conversion of ω-6 FAs to ω-3 FAs improves PTOA severity remains to be determined. The present Example examines the hypothesis that diet-induced obesity results in premature cell senescence in mice, and that overexpression of the Fat-1 gene prevents this phenomenon by reducing systemic inflammation and increasing the number of anti-inflammatory macrophages, in the context of obesity and OA.

Methods

All animal procedures were approved by the IACUC. For in vivo studies, five-week-old male C57BL/6 mice were fed either Control (10% kcal fat) or high-fat diet rich in ω-6 FAs (HFD) (60% kcal fat). At 8 weeks of age, either an AAV8-mediated fat-1 (FAT-1) or luciferase (LUC) control gene vector, both driven by the CMV promoter, were delivered via tail vein at a dose of $5\times10^{11}$ vg/mouse. One group received the surgical destabilization of the medial meniscus (DMM) on the left hindlimb at 16 weeks of age to induce knee OA (FIG. 5A) and was euthanized at 28 weeks of age. Another group of mice was aged up to 52 weeks with no surgical intervention. Freshly isolated adipose tissue (AT) biopsies and cryosections were stained for senescence-associated-β-galactosidase (SA-β-gal), and paraffin fixed AT sections were subject to IHC with anti-CD206 antibody. The expression of p21 protein was also assessed by Western Blot in whole AT specimens. Knee joints were labeled for anti-p16INK4a and CD206 by IHC. To understand the mechanism of reduced chondrocyte senescence mediated by AAV8-fat-1 delivery during obesity, an in vitro experiment was conducted by co-culturing primary young mouse chondrocytes with conditioned media obtained from bone marrow macrophages from aged Control or HFD mice expressing either LUC or FAT-1. The cellular reactive oxygen species (ROS) assay (DCFDA) was conducted after 3 days of cell co-culture, and flow cytometry analysis for p16INK4a expression along with SA-β-gal assay were conducted after 7 days of cell co-culture. Statistical analysis was performed using the Mann-Whitney U test.

Results

Figure 6:
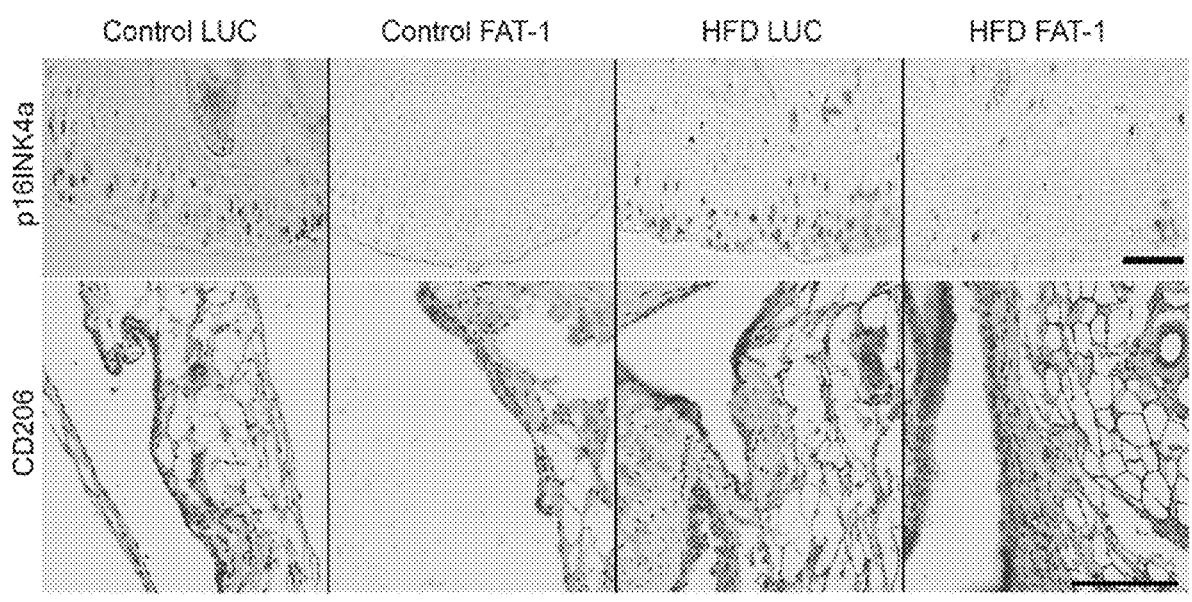
FIG. 6 shows cartilage senescence and synovial macrophages content as representative anti-p16INK4a and CD206 IHC of paraffin section from DMM-operated knee. scale bars=100 μm
Figure 7A:
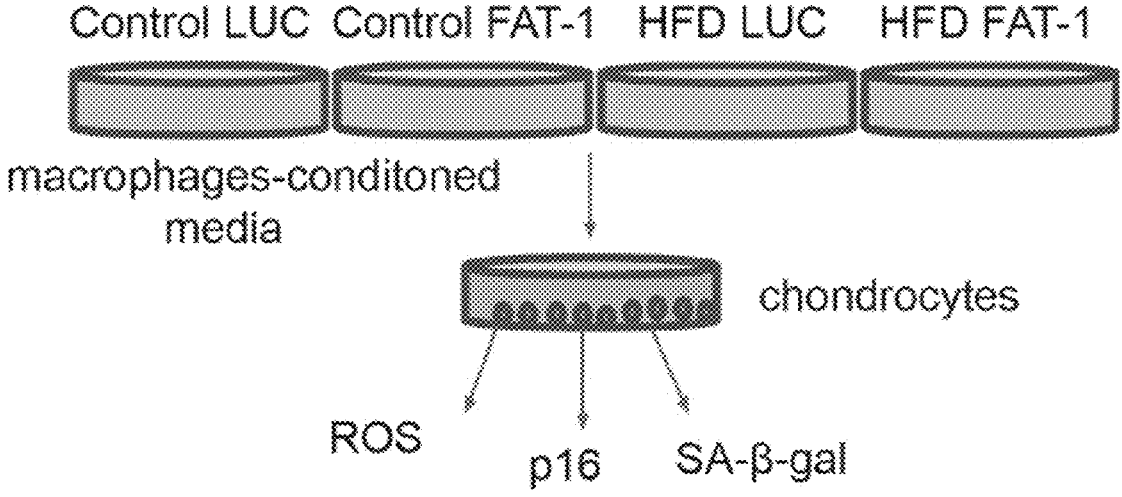
FIG. 7A-7C show in vitro analysis of chondrocyte senescence.
Figures 7B, 7C:
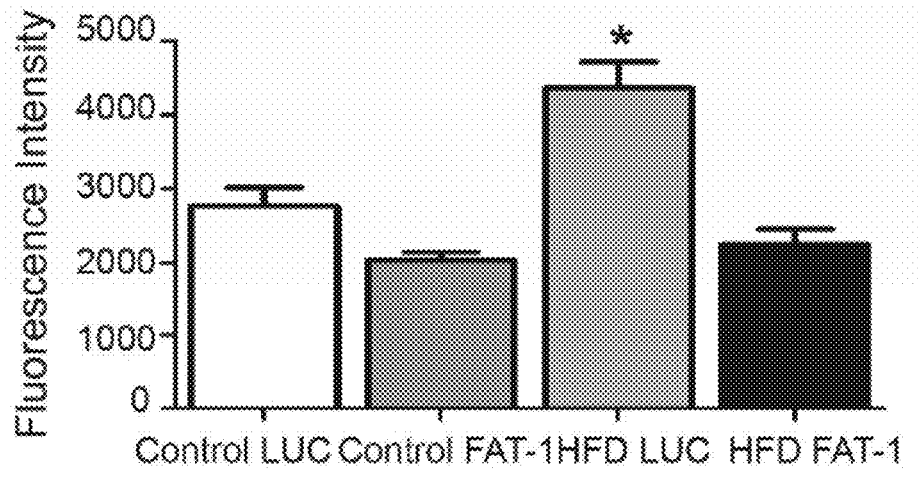

AAV8-fat-1 overexpression significantly reduced obesity-induced cell senescence, indicated by decreased content of β-gal positive cells and decreased expression of p21 protein in AT (FIG. 5B-5C). It was also found that the reduction in AT cell senescence correlated with increased content of anti-inflammatory $CD206^+$ M2-like macrophages in HFD animals. In DMM-operated joints, obesity increased cell senescence (as indicated by increased p16INK14a immunostaining), which was mitigated in mice receiving fat-1 gene therapy (FIG. 6). Interestingly, an increase in anti-inflammatory M2-like macrophages in the synovium of HFD-FAT1 mice was found, indicated by increased CD206 staining (FIG. 6). In co-culture experiments, media derived from macrophages obtained from obese mice (HFD-LUC) increased the content of ROS, p16INK4α, and SA-β-gal expression in chondrocytes, and this process was eliminated in macrophages from mice overexpressing fat-1 (HFD-FAT1) (FIG. 7A-7C).

Cell senescence, an irreversible cell cycle arrest, has been shown to play an important role in both normal and altered physiological processes. This complex cellular response has been reported to be affected by aging and nutritional compounds of the diet. It was found that a high-fat obesogenic diet causes premature cell senescence in both AT and cartilage, while fat-1 gene therapy mitigates this process. It was also observed an increase in anti-inflammatory M2-like macrophages present in mice that received fat-1 gene therapy. Previous studies have reported increased presence of M1-like macrophages in obesity-induced OA, and that aging affects the ability of macrophages to maintain an anti-inflammatory profile. Increased production of ROS is one of the primary mechanisms believed to induce cellular senescence. Through co-culture studies, it was found that macrophages isolated from aging obese mice promote chondrocyte senescence by increasing ROS production, pINK4a, and SA-β-gal expression; moreover, fat-1 gene therapy significantly diminished this effect.

Modulation of the ω-6:ω-3 FA ratio through gene therapy prevented obesity-associated cell senescence and may potentially provide a therapeutic approach for treating OA.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The term "about" or "approximately" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A method of reducing osteoarthritis (OA) in a subject in need thereof, the method comprising: administering an adeno-associated virus serotype 8 (AAV8) vector comprising a nucleic acid encoding fat-1 or administering an engineered probiotic composition to the subject, wherein the engineered probiotic expresses fat-1.

2. The method of claim 1, wherein the subject exhibits a reduction in the level of an inflammatory cytokine selected from the group consisting of IL-1β, IL-1α, TNFα, or IL-6, relative to an untreated subject or the same subject prior to administration of the viral vector or engineered probiotic.

3. The method of claim 1, wherein the subject exhibits an increase in the number of M2-macrophages relative to an untreated subject or the same subject prior to administration of the viral vector or engineered probiotic.

4. A method of reducing a condition selected from post-traumatic osteoarthritis and joint degeneration in a subject in need thereof, the method comprising: administering an adeno-associated virus serotype 8 (AAV8) vector comprising a nucleic acid encoding fat-1 or administering an engineered probiotic composition to the subject, wherein the engineered probiotic expresses fat-1.

5. The method of claim 4, wherein the condition is osteoarthritis.

6. The method of claim 5, wherein bone microstructure is improved.

7. The method of claim 5, wherein the severity of osteoarthritis is reduced.

8. The method of claim 4, wherein the condition is joint degeneration.

9. The method of claim 4, wherein the engineered probiotic comprises one or more of: Escherichia, Lactobacillus, Bifidobacterium, Lactococcus, Bacteroides, Clostridium, and Streptococcus.

10. The method of claim 4, wherein the nucleic acids encoding fat-1 are codon optimized.

11. The method of claim 4, wherein the probiotic is a non-pathogenic probiotic bacteria.

12. The method of claim 11, wherein the non-pathogenic probiotic bacteria are transformed with nucleic acids encoding for fat-1 gene to generate the engineered probiotics.

13. The method of claim 4, wherein the nucleic acid sequence coding for fat-1 comprise additional nucleic acid sequences for antibiotic selection, genetic activation, stability, or survival.

14. The method of claim 4, wherein the subject is obese.

15. The method of claim 4, wherein the subject is a human, livestock, or companion animal.

16. The method of claim 1, wherein the engineered probiotic comprises one or more of: Escherichia, Lactobacillus, Bifidobacterium, Lactococcus, Bacteroides, Clostridium, and Streptococcus.

17. The method of claim 1, wherein the nucleic acids encoding fat-1 are codon optimized.

18. The method of claim 1, wherein the probiotic bacteria is a non-pathogenic probiotic bacteria and wherein the non-pathogenic probiotic bacteria are transformed with nucleic acids encoding for fat-1 gene to generate the engineered probiotics.

19. The method of claim 1, wherein the subject is obese.

* * * * *